US008740883B2

(12) United States Patent
Skora et al.

(10) Patent No.: US 8,740,883 B2
(45) Date of Patent: Jun. 3, 2014

(54) DETACHABLE HANDLE MECHANISM FOR USE IN INSTRUMENT POSITIONING

(75) Inventors: Brooke Skora, San Diego, CA (US); Jose Jacquez, Spring Valley, CA (US); How-Lun Chen, San Diego, CA (US)

(73) Assignee: Carefusion 2200, Inc., San Diego, CA (US)

( * ) Notice: Subject to any disclaimer, the term of this patent is extended or adjusted under 35 U.S.C. 154(b) by 554 days.

(21) Appl. No.: 12/895,411

(22) Filed: Sep. 30, 2010

(65) Prior Publication Data

US 2012/0083768 A1 Apr. 5, 2012

(51) Int. Cl.
*A61B 17/00* (2006.01)
*A61B 19/10* (2006.01)

(52) U.S. Cl.
USPC .............................................. 606/1; 128/851

(58) Field of Classification Search
USPC ............... 606/1; 128/849, 851; 600/101, 102, 600/131, 133
See application file for complete search history.

(56) References Cited

U.S. PATENT DOCUMENTS

| 594,692 | A | 11/1897 | Henneberg |
|---|---|---|---|
| 3,923,166 | A | 12/1975 | Fletcher |
| 4,414,962 | A | 11/1983 | Carson |
| 4,750,475 | A | 6/1988 | Yoshihashi |
| 5,201,908 | A | 4/1993 | Jones |
| 5,361,583 | A | 11/1994 | Huitema |
| 5,441,042 | A | 8/1995 | Putman |
| 5,624,398 | A | 4/1997 | Smith et al. |
| 5,762,458 | A | 6/1998 | Wang et al. |
| 5,792,135 | A | 8/1998 | Madhani et al. |
| 5,807,240 | A | 9/1998 | Muller et al. |
| 5,807,377 | A | 9/1998 | Madhani et al. |
| 5,808,665 | A | 9/1998 | Green |
| 5,855,583 | A | 1/1999 | Wang et al. |
| 5,890,781 | A | 4/1999 | Ryder |
| 5,976,122 | A | 11/1999 | Madhani et al. |
| 6,096,004 | A | 8/2000 | Meglan et al. |
| 6,149,252 | A | 11/2000 | Browning |
| 6,301,526 | B1 | 10/2001 | Kim et al. |
| 6,364,888 | B1 | 4/2002 | Niemeyer et al. |

(Continued)

FOREIGN PATENT DOCUMENTS

WO WO-9740759 11/1997

OTHER PUBLICATIONS

ISA/KR, International Search Report and Written Opinion for International Application No. PCT/US2011/054101, 17 pages, Apr. 18, 2012.

*Primary Examiner* — Ahmed Farah
(74) *Attorney, Agent, or Firm* — Arent Fox LLP

(57) ABSTRACT

A detachable control handle of a surgical device for use in positioning an instrument for use in a surgical procedure. The detachable control handle comprises: a handle assembly configured for communicating with a mechanical positioning mechanism via a connector, wherein said mechanical positioning mechanism is configured to couple with said instrument outside of a patient's body and to move said instrument relative to said patient's body, said handle assembly comprising: a control handle; a detaching mechanism coupled with said control handle, said detaching mechanism configured for detachably coupling said control handle with said mechanical positioning mechanism, wherein said control handle and said mechanical positioning mechanism are sealingly coupled with a first and second portion of a drape interface mechanism of a sterile drape, respectively, wherein said sterile drape is configured for isolating a portion of said surgical device within a sterile environment.

13 Claims, 25 Drawing Sheets

(56) References Cited

U.S. PATENT DOCUMENTS

| | | |
|---|---|---|
| 6,607,475 B2 | 8/2003 | Doyle et al. |
| 7,331,967 B2 | 2/2008 | Lee et al. |
| 7,470,268 B2 | 12/2008 | Doyle et al. |
| 7,865,266 B2 | 1/2011 | Moll et al. |
| 8,105,319 B2 | 1/2012 | Doyle et al. |
| 2002/0128633 A1 | 9/2002 | Brock et al. |
| 2004/0049205 A1 | 3/2004 | Lee et al. |
| 2004/0172041 A1 | 9/2004 | Gresham et al. |
| 2004/0237785 A1 | 12/2004 | Neri |
| 2005/0043718 A1 | 2/2005 | Madhani et al. |
| 2005/0090811 A1 | 4/2005 | Doyle et al. |
| 2005/0169726 A1 | 8/2005 | McClure |
| 2005/0171470 A1 | 8/2005 | Kucklick et al. |
| 2006/0079884 A1 | 4/2006 | Manzo et al. |
| 2006/0161137 A1 | 7/2006 | Orban et al. |
| 2006/0235436 A1 | 10/2006 | Anderson et al. |
| 2007/0123798 A1 | 5/2007 | Rahamimov |
| 2007/0123855 A1 | 5/2007 | Morley et al. |
| 2007/0137371 A1 | 6/2007 | Devengenzo et al. |
| 2007/0156121 A1 | 7/2007 | Millman et al. |
| 2007/0239172 A1 | 10/2007 | Lee et al. |
| 2007/0267026 A1 | 11/2007 | Grant-Jennings |
| 2008/0033453 A1 | 2/2008 | Brock et al. |
| 2008/0065098 A1 | 3/2008 | Larkin |
| 2008/0188715 A1 | 8/2008 | Fujimoto |
| 2009/0030443 A1 | 1/2009 | Buser et al. |
| 2009/0105727 A1 | 4/2009 | Doyle et al. |
| 2009/0182351 A1 | 7/2009 | Malinowski |
| 2009/0248039 A1 | 10/2009 | Cooper et al. |
| 2009/0294313 A1 | 12/2009 | Pacey et al. |
| 2010/0063359 A1 | 3/2010 | Okoniewski |
| 2010/0241136 A1 | 9/2010 | Doyle et al. |
| 2011/0178531 A1 | 7/2011 | Caputo et al. |
| 2011/0319911 A1 | 12/2011 | Conner et al. |
| 2012/0010611 A1 | 1/2012 | Krom et al. |
| 2012/0010628 A1 | 1/2012 | Cooper et al. |
| 2012/0080041 A1* | 4/2012 | Skora et al. .................. 128/851 |
| 2012/0083799 A1 | 4/2012 | Chen et al. |
| 2012/0118098 A1 | 5/2012 | Doyle et al. |
| 2012/0239060 A1* | 9/2012 | Orban, III .................. 606/130 |

* cited by examiner

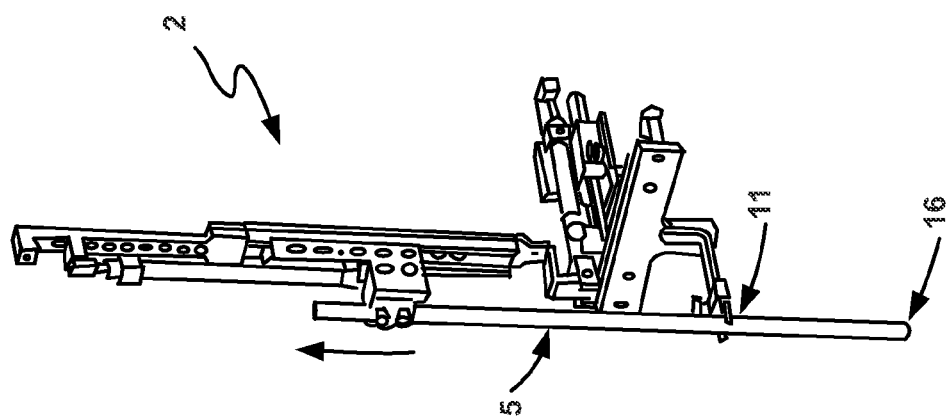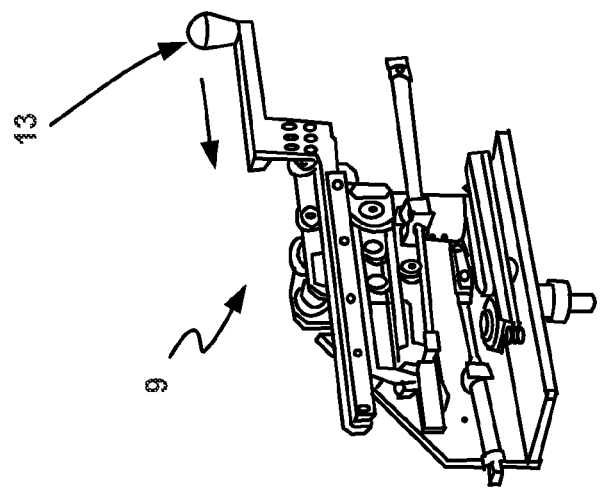
FIG. 5F

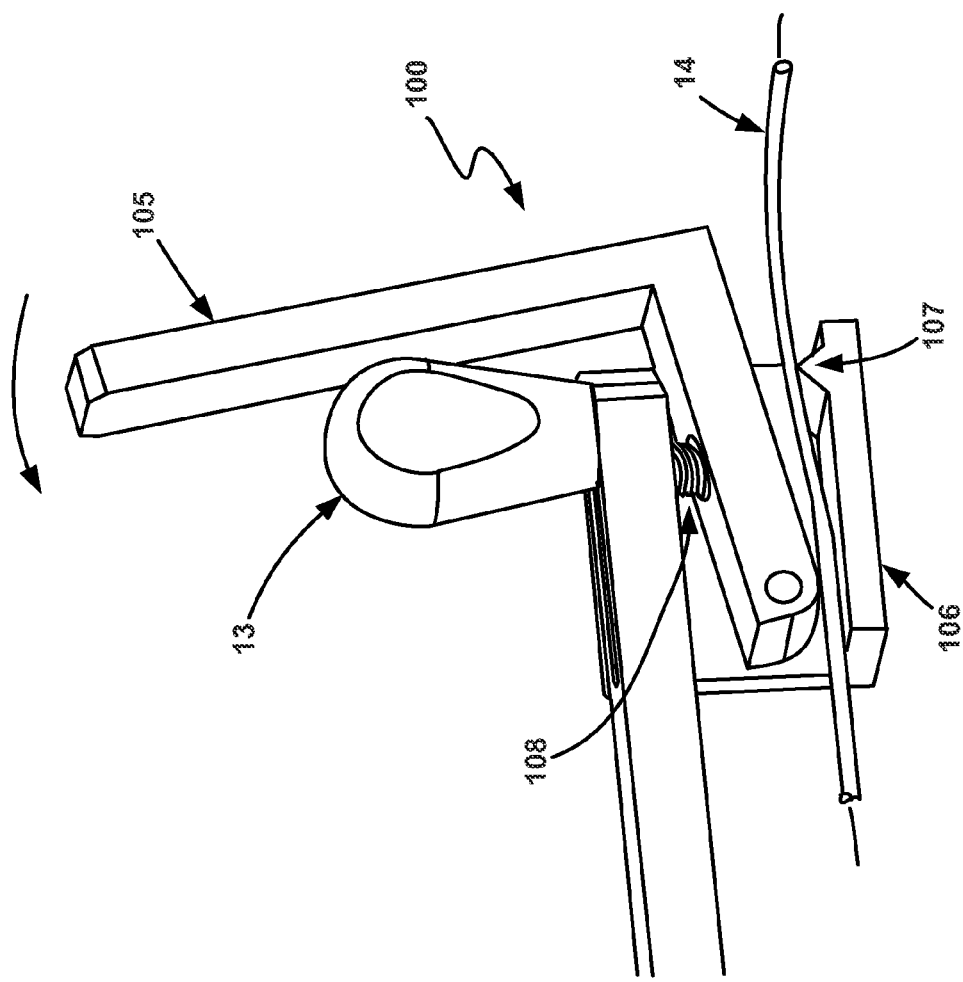

DETACHABLE HANDLE MECHANISM FOR USE IN INSTRUMENT POSITIONING

RELATED APPLICATION

International Patent Publication Number 2008/070685 A2 entitled Instrument Positioning/Holding Devices, by Mark C. Doyle and Jimmy C. Caputo, assigned to the assignee of the present technology, filed Dec. 4, 2007.

FIELD

The technology relates generally to surgical instruments. More particularly, the technology relates to devices for positioning/holding a surgical instrument and methods of positioning/holding a surgical instrument.

BACKGROUND

Blade Endoscopic surgical procedures are performed using long slender surgical instruments inserted into the patient through small incisions. In order to visualize the surgical site an endoscope is also inserted into the patient through another incision. A camera is attached to the endoscope, and the image is projected onto a nearby video display, which the surgeon looks at to monitor his/her activities inside the patient.

In order to permit the surgeon to use both hands for the surgery the endoscope is held in the desired position by an assistant, a stationary adjustable arm, or a voice controlled robotic positioning device. All three have significant drawbacks. The assistant, besides being a costly paid employee, can be difficult to communicate with, can get tired, and can lose concentration and let the endoscope position drift. The stationary adjustable arms require that the surgeon reach over to adjust them with two hands, wasting valuable time and disrupting the procedure. The voice-controlled robotic positioning devices are expensive, require significant set-up effort, and often require too much time communication time.

During many procedures an assistant also positions and holds a retracting instrument in order to push tissue or organs out of the way of the surgeon's instrument. The same issues of communication, concentration, and fatigue are present in this task also.

BRIEF DESCRIPTION OF THE DRAWINGS

The accompanying drawings, which are incorporated in and form a part of this specification, illustrate embodiments of the present technology and, together with the description, serve to explain principles discussed below:

FIGS. 5a-f show a schematic view of the relationship between motions of an embodiment of the control mechanism and an embodiment of the positioning mechanism, in accordance with the present technology.

FIGS. 11a-c show a close-up view of an embodiment of the control mechanism that has an embodiment of a brake system, in accordance with the present technology.

The drawings referred to in this description should not be understood as being drawn to scale unless specifically noted.

DESCRIPTION OF EMBODIMENTS

Reference will now be made in detail to embodiments of the present technology, examples of which are illustrated in the accompanying drawings. While the present technology will be described in conjunction with various embodiment(s), it be understood that they are not intended to limit the present technology to these embodiments. On the contrary, the present technology is intended to cover alternatives, modifications and equivalents, which may be included within the spirit and scope of the various embodiments as defined by the appended claims.

Certain embodiments of the technology will now be described with reference to the figures.

Figure 1:
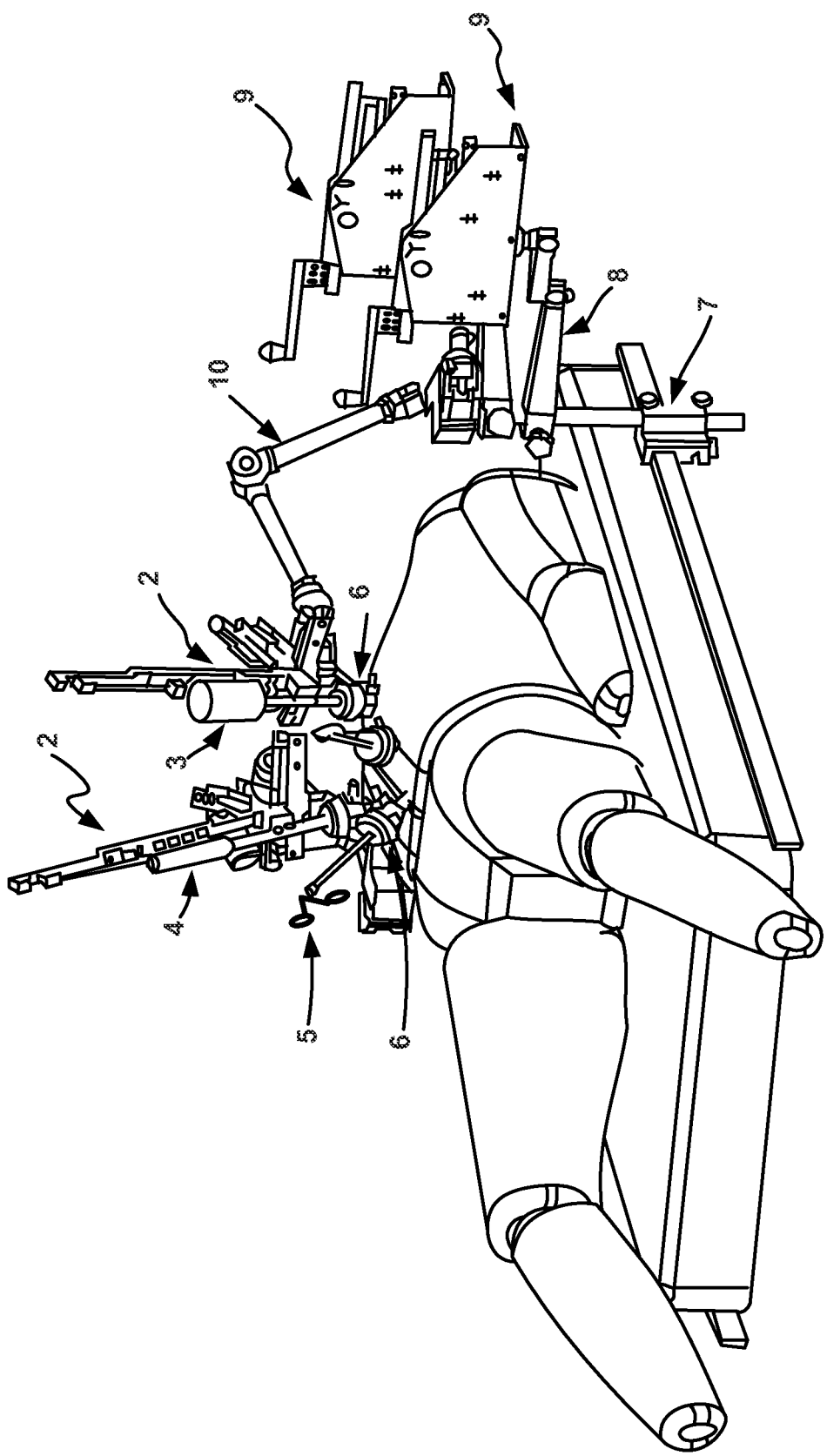
FIG. 1 shows a perspective view of an embodiment of the present technology used in conjunction with various surgical devices during a surgical procedure.

Referring to FIG. 1, numerous surgical devices are shown inserted into a patient on an operating bed. Laparoscopic instruments 5 are inserted through access ports 6 to cut, suture, manipulate tissue, etc. An endoscope/camera assembly 3, used to visualize the surgical site, is also inserted through an access port 6, and is held in place by the positioning mechanism 2. The positioning mechanism 2 is held by an adjustable arm 10, which is mounted on a support structure 7. A control handle 9 is mounted on a support bracket 8. In use, the user controls the position of the endoscope/camera 3 by manipulating the control handle 9, which causes the positioning mechanism 2 to move the endoscope/camera 3 to the desired position. Once the user stops manipulating the control handle 9 the positioning mechanism 2 stops moving and holds the endoscope/camera 3 in the new position.

Other instruments can also be positioned and held in this way. For example, a retractor 4 is shown attached to a positioning mechanism 2 in the same way as the endoscope/camera. The retractor 4 is pushed against organs or tissue to hold them out of the surgeon's way. The user manipulates the appropriate control handle 9 to cause the positioning mechanism 2 to move the retractor 4 in the appropriate direction. Once the user stops moving the control handle 9 the positioning mechanism 2 stops moving and holds the retractor 4 in the desired position. Of course any other instrument useful in a surgical procedure could be held and manipulated by embodiments of the devices of the present technology. The variety of devices which can be thus moved and held by the positioning mechanism and control handle are referred to below as "instrument(s)". The instruments may be permanently coupled to the positioning mechanism 2 or interchangeable attached. In some embodiments, an instrument is coupled to the positioning mechanism 2 prior to the instrument's insertion into the patient's body. In other embodiments, the instrument is first manually inserted into the body and positioned followed by coupling to the positioning mechanism 2. In some embodiments, the positioning mechanism is located outside of the patient's body and couples to an instrument outside of the patient's body.

With the positioning mechanism 2 and control handle 9 arrangement described above the surgeon can reposition and hold various instruments without the need for an assistant—thereby avoiding the problems of communicating with that assistant, or the problems of fatigue and loss of attention of the assistant.

Figure 2:
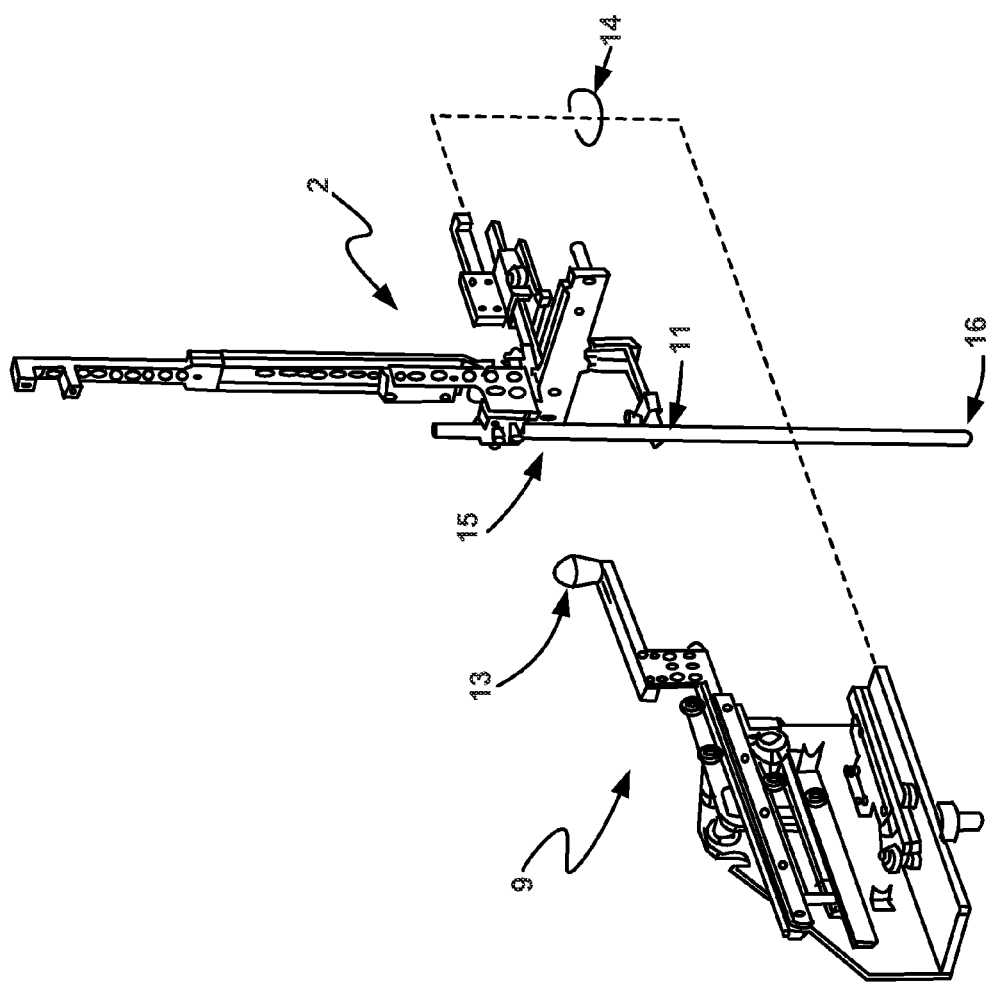
FIG. 2 shows a schematic view of an embodiment of the positioning mechanism and an embodiment of the control mechanism connected by a mechanical force-transmitting connector, in accordance with the present technology.

FIG. 2 shows an embodiment of the positioning mechanism 2 and an embodiment of the control mechanism, control handle 9, connected by a mechanical force-transmitting connector 14. This mechanical force-transmitting connector 14 transmits force signals from the control handle 9 to the position mechanism 2, allowing the user to move the positioning mechanism 2 by manipulating the control handle 9. As discussed below, the mechanical force-transmitting connector 14 can be hydraulic, cable-pulley, push-pull cable, or other mechanical means.

The control mechanism can have any configuration which permits the surgeon to effectively manipulate the positioning mechanism. In the depicted embodiment, the control mechanism is a particular control handle 9. However, other control mechanisms are contemplated. By way of non-limiting example, the control mechanism may have a glove-like configuration that engages the users arm, hand, and fingers.

In use, the user moves the control handle 9 by pushing knob 13 in the desired direction. Force signals are transmitted from the control handle 9 to the positioning mechanism 2 via the mechanical force-transmitting connector 14, causing the positioning mechanism 2 to move in response. The instrument 15 moves in several axes. In a preferred embodiment the instrument pivots about the point 11 where it enters the patient. The patient's tissue at point 11 can serve as the pivot, or a pivot bearing (not shown) can be provided to cause the instrument 15 to pivot about point 11. The positioning mechanism 2 pushes the instrument 15 forward-backward, side-to-side, or any combination of these two. The instrument 15, constrained at point 11 by either the patient's tissue or a pivot bearing (not shown), tilts about point 11, with the result that the distal tip of the instrument 16 moves to a new position inside of the patient. The preferred embodiment also contains an extend axis which permits the user to extend or retract the distal end of the instrument 16.

Figure 3:
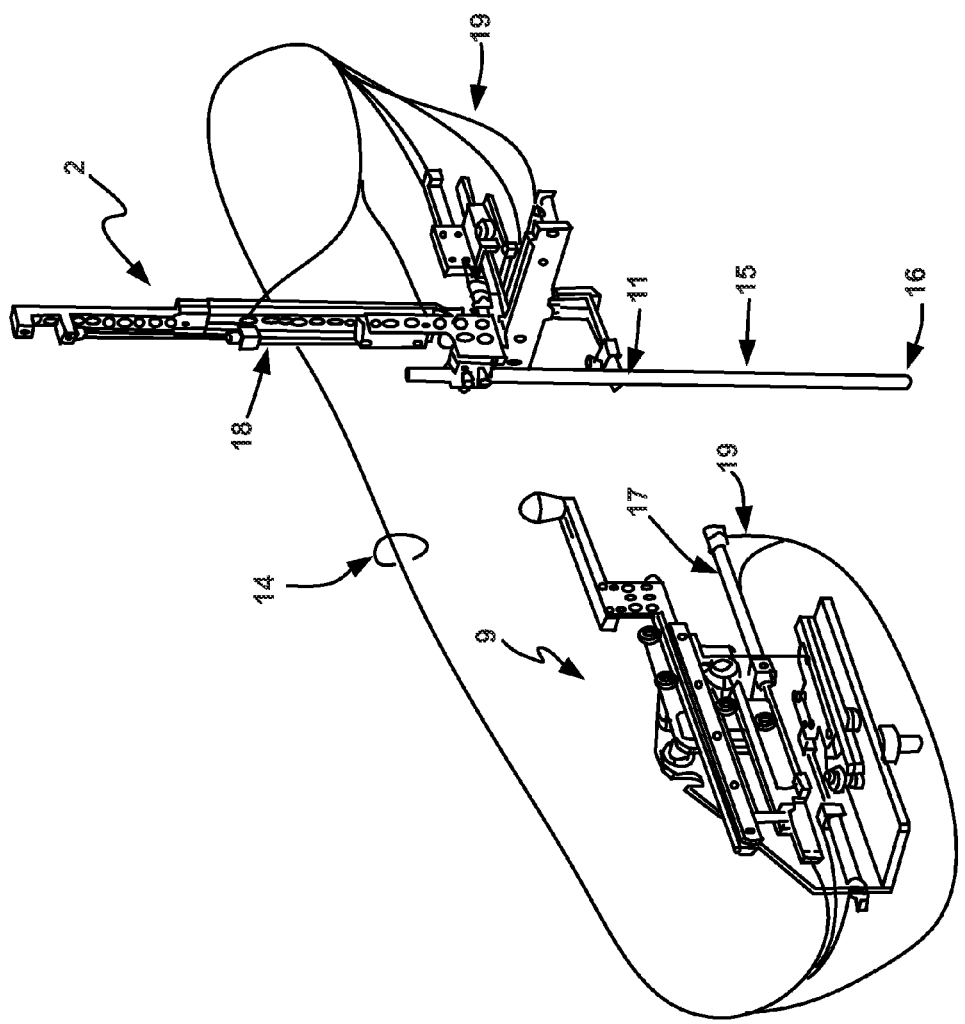
FIG. 3 shows a schematic view of an embodiment of the positioning mechanism and an embodiment of the control mechanism connected by a hydraulic mechanical-force-transmission connector, in accordance with the present technology.

Referring to FIG. 3, a preferred embodiment is shown in which the mechanical-force-transmission connection is hydraulic. Motions of the control handle 9 cause hydraulic fluid (not shown) to travel through tubing to the positioning mechanism 2, which responds to tilt and/or extend/retract the instrument 15 about point 11, thereby repositioning the distal tip 16 of the instrument 15 inside the patient. Conventional hydraulic systems, employing cylinders, pumps, valves, and reservoirs can be used. A preferred hydraulic method is shown in FIG. 3. Control hydraulic cylinder(s) 117 in the control handle 9 are connected in a closed-loop circuit to slave hydraulic cylinder(s) 18 in the positioning mechanism 2 via tubing 19. When the user moves the control handle 9 to a new position, the shaft of the control cylinder 17 is pushed or pulled, thereby displacing hydraulic fluid in the control cylinder 17. This hydraulic fluid is forced through tubing 19 to the responding slave cylinder 18 in the positioning mechanism 2, causing the shaft of the slave cylinder 18 to move. This movement is used to tilt and/or extend/retract the instrument.

Figure 4A:
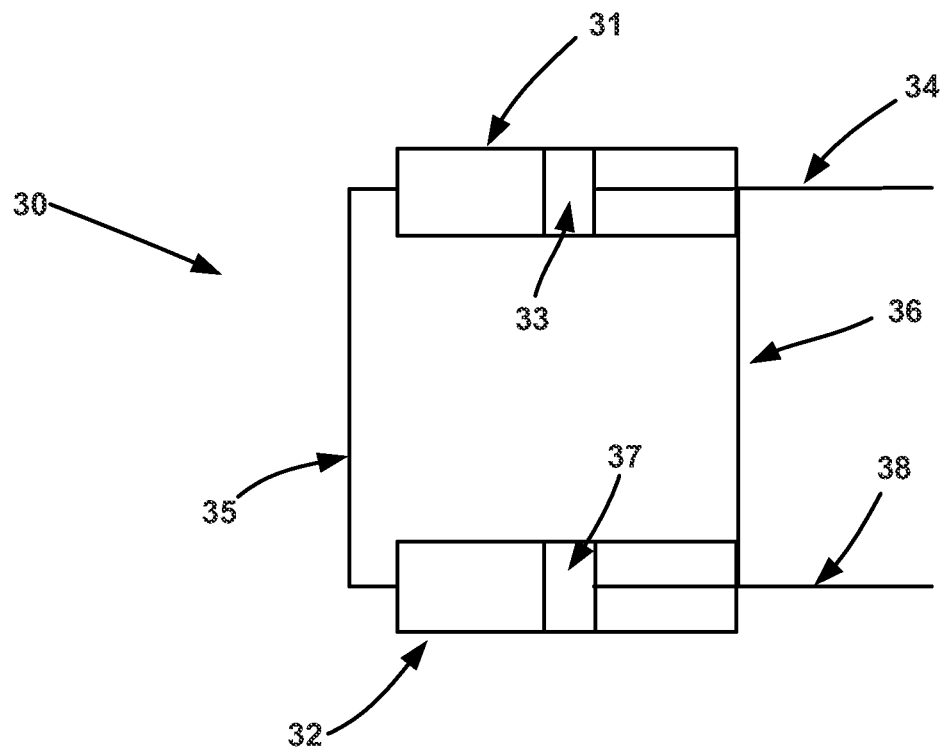
FIGS. 4a-4c show a schematic view of an embodiment of a closed-loop hydraulic system, in accordance with the present technology.
Figure 4B:
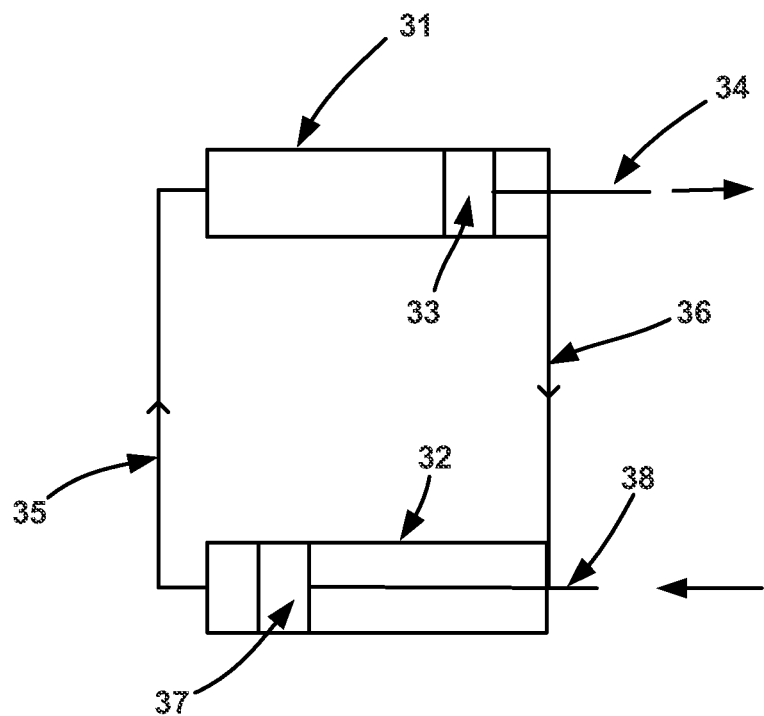
Figure 4C:
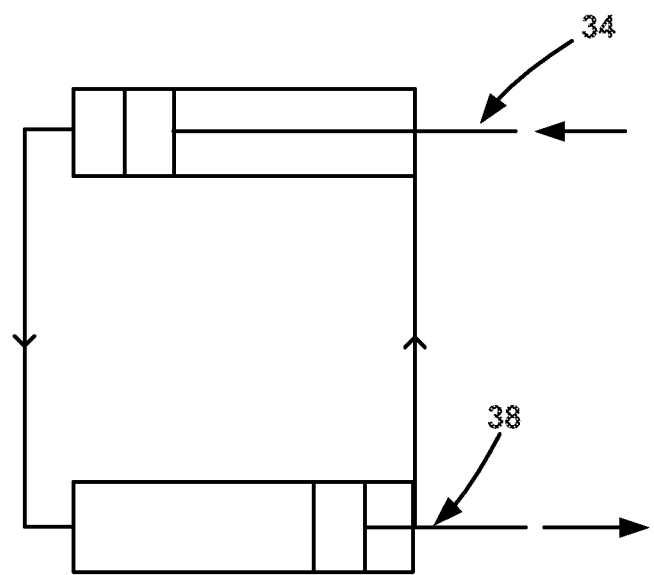

FIGS. 4a-4c. show this action in schematic form. A basic closed-loop hydraulic circuit 30 is shown in FIG. 4a. The control cylinder 31 contains a piston 33 which is connected to a shaft 34. Similarly, the slave cylinder 32 contains a piston 37 connected to a shaft 38. The back side of each cylinder is connected to the other by tubing 35. Similarly, the front side of each cylinder is connected to the front of the other by means of tubing 36.

As shown in FIG. 4b, the shaft 34 of the control cylinder 31, located in the control handle 9, is pulled to the right, pulling the piston 33 to the right. This action causes hydraulic fluid to travel from the front of control cylinder 31 to the front of slave cylinder 32 via tubing 36. This forces the shaft 38 and piston 37 in slave cylinder 32 to move to the left. This drives hydraulic fluid from the back of slave cylinder 32 to the back of control cylinder 31 via tubing 35. The motion of slave shaft 38 is used in the positioning mechanism 2 to reposition the tip 16 of the instrument to the desired location.

FIG. 4c shows the reverse motion, in which the control shaft 34 is moved to the left, causing the slave shaft 38 to move to the right.

Figure 5A:
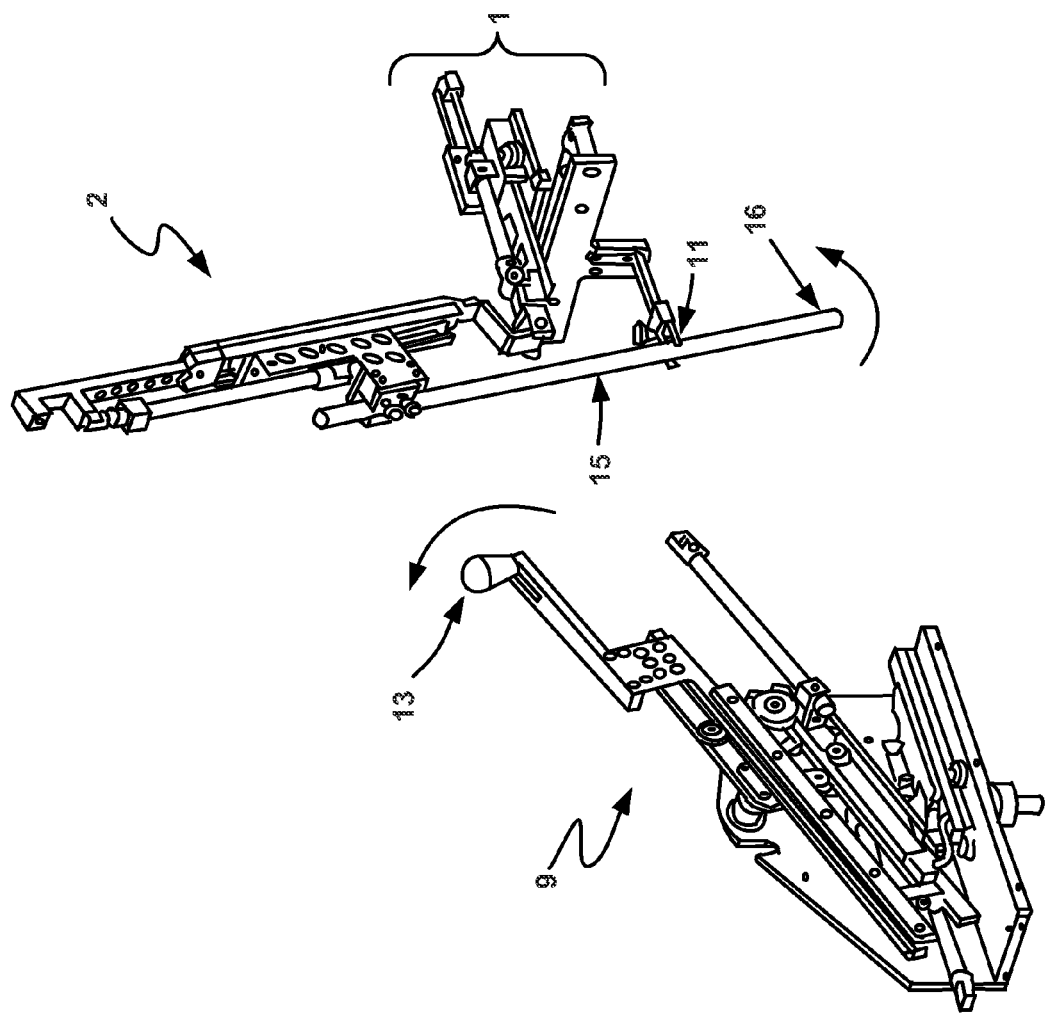
Figure 5B:
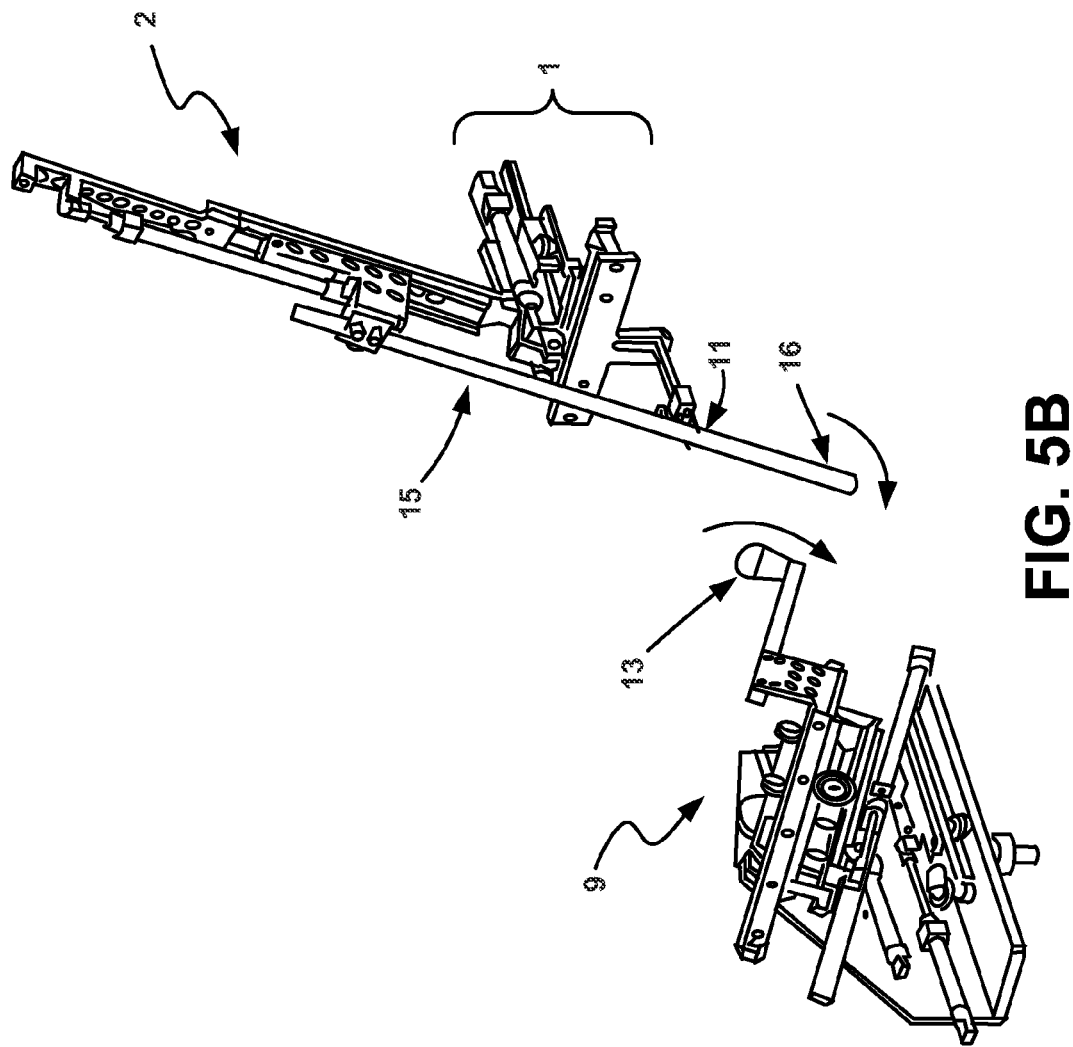
Figure 5C:
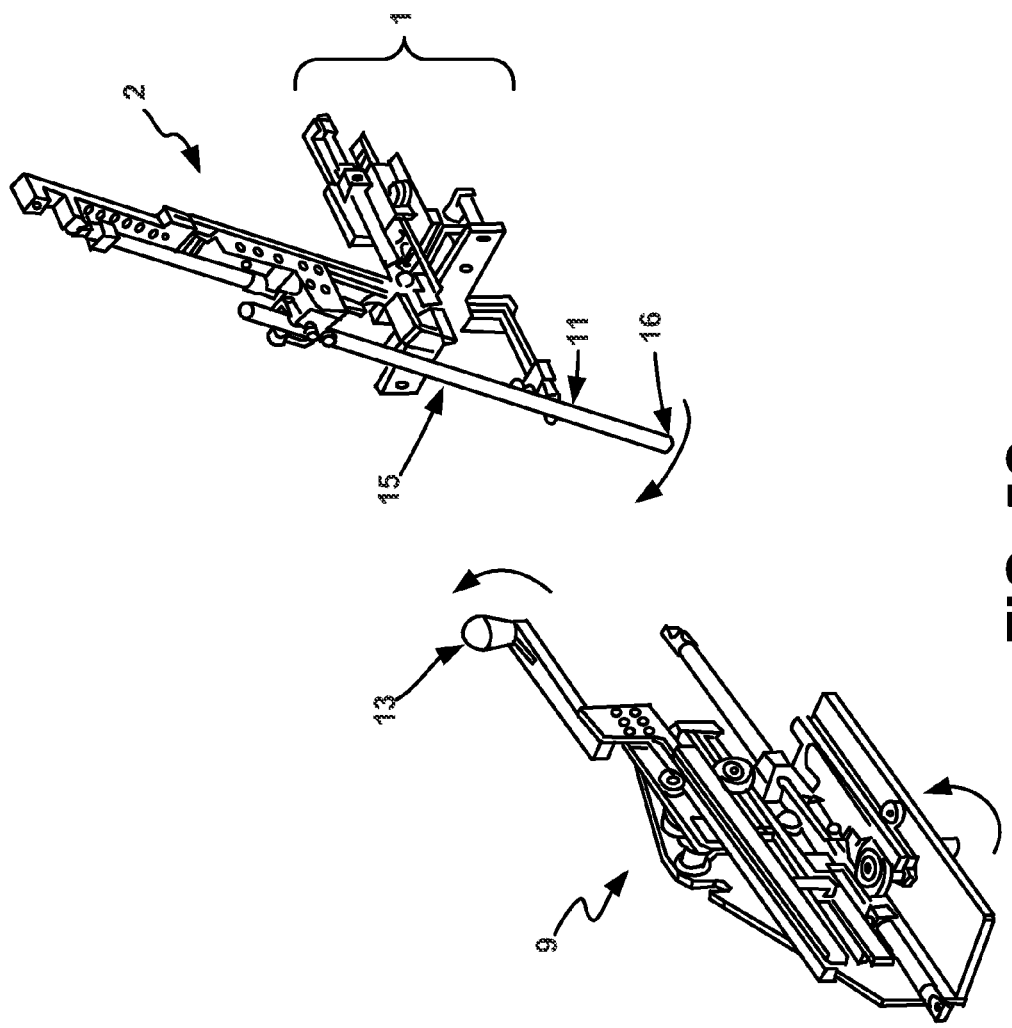
Figure 5D:
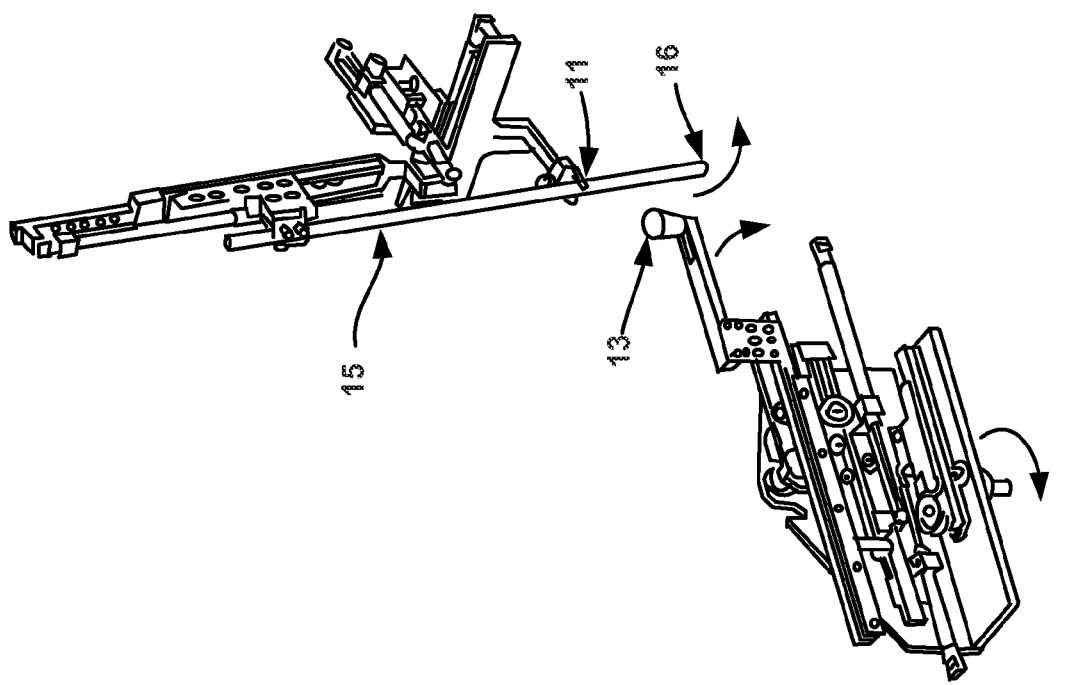
Figure 5E:
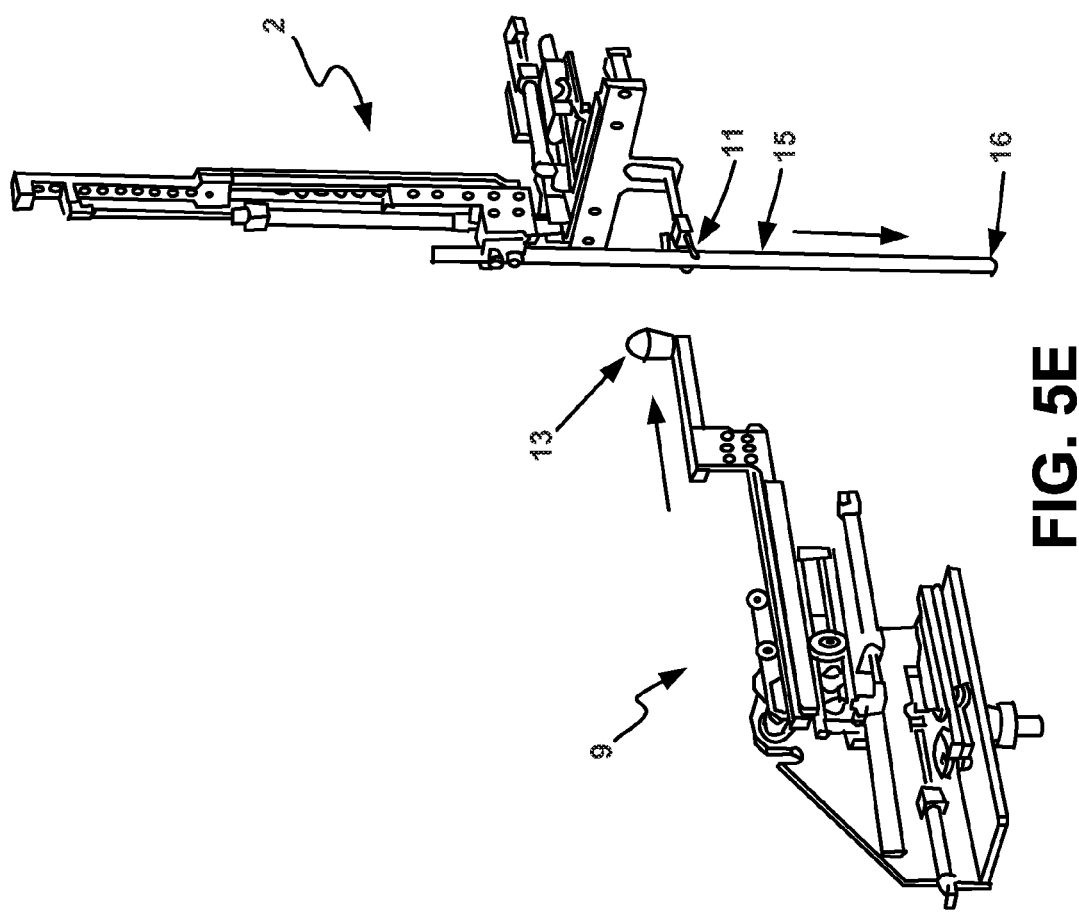

FIGS. 5a-f show the relationship between motions of the control handle 9 and an embodiment of the positioning mechanism 2. In FIG. 5a the knob 13 of control handle 9 has been pulled upward, forcing hydraulic, fluid to travel between control cylinders in control handle 9 and slave cylinders in positioning mechanism 2, thereby causing positioning mechanism 2 to tilt the instrument 15 about point 11 and thus more the distal tip 16 of instrument 15 back in relation to the housing 1 of the positioning mechanism 2. FIG. 5b similarly shows the knob 13 pushed downward, causing tip 16 to move away from the housing 1 of positioning mechanism 2. FIG. 5c shows the knob 13 moved to the left, thereby driving tip 16 to the right relative to housing 1 of positioning mechanism 2. Similarly FIG. 5d shows the knob 13 moved to the right, thereby driving tip 16 to the left relative to housing 1 of positioning mechanism 2. In FIG. 5e the knob 13 is pushed forward to extend tip 16 further into the patient, and similarly FIG. 5f shows the knob pulled backward to retract tip 16 from the patient.

Figure 6A:
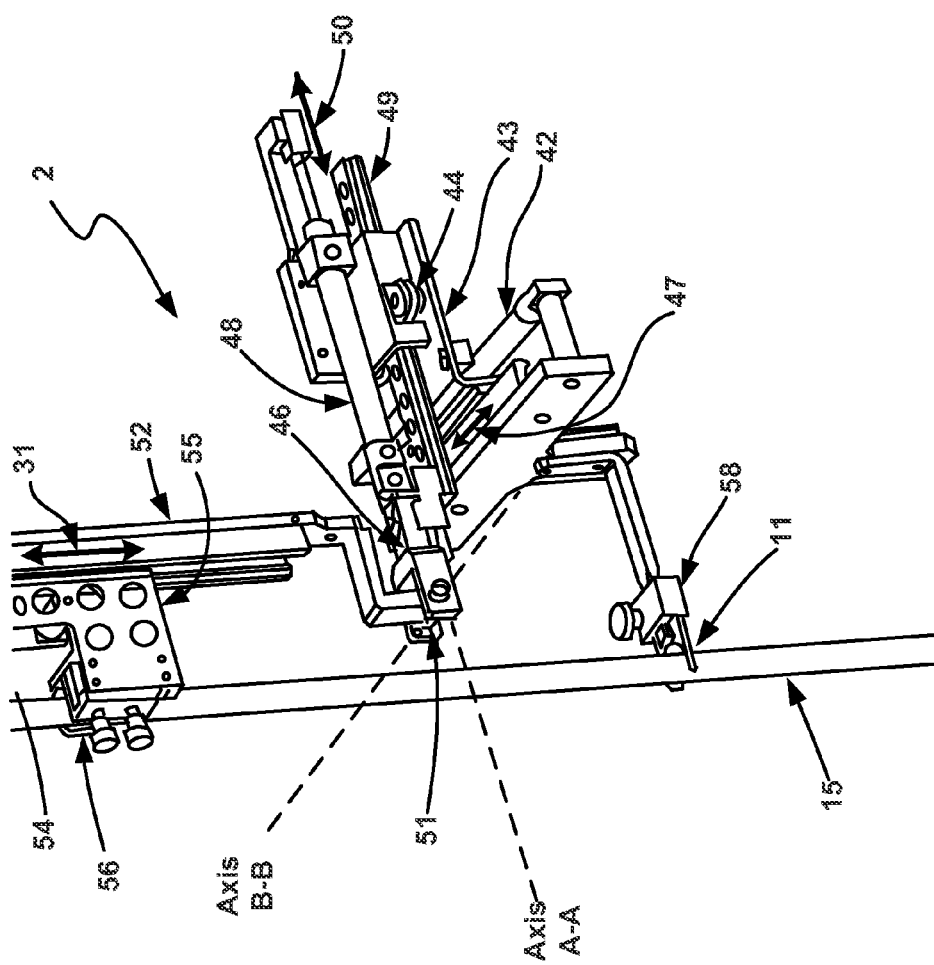
FIGS. 6a-c show a close-up schematic view of an embodiment of the positioning mechanism, in accordance with the present technology.

Referring to FIG. 6a, more detail of an embodiment of the positioning mechanism is provided. All three of the motion axes comprise a slave cylinder and guide device. The side-to-side motion is achieved by motion of slave cylinder 42, which pushes/pulls tilt slide assembly 44, which is free to move side-to-side as shown by arrow 47. This motion is transmitted to instrument slide assembly 52 by a non-rigid pivot bearing 46. This pivot bearing 46 allows the instrument slide assembly 52 to rotate about axis A-A and automatically assume the correct angle to permit the instrument 15 to pivot about point 11. The forward/backward motion is achieved by motion of slave cylinder 48, which pushes and pulls guide device 49 along rollers 44 as shown by arrow 50. The motion of guide device 49 is transmitted to instrument slide assembly 52 via non-rigid pivot bearing 51. This pivot bearing 51 allows the instrument slide assembly 52 to rotate about axis B-B and automatically assume the correct angle to permit the instrument 15 to pivot about point 11. The extend/retract motion is achieved by motion of slave cylinder 54, which pushes/pulls extend slide 55 in the direction indicated by arrow 57. Instrument 15 is attached to extend slide 55 by clamp 56, and thus extended or retracted in the patient.

Figure 6B:
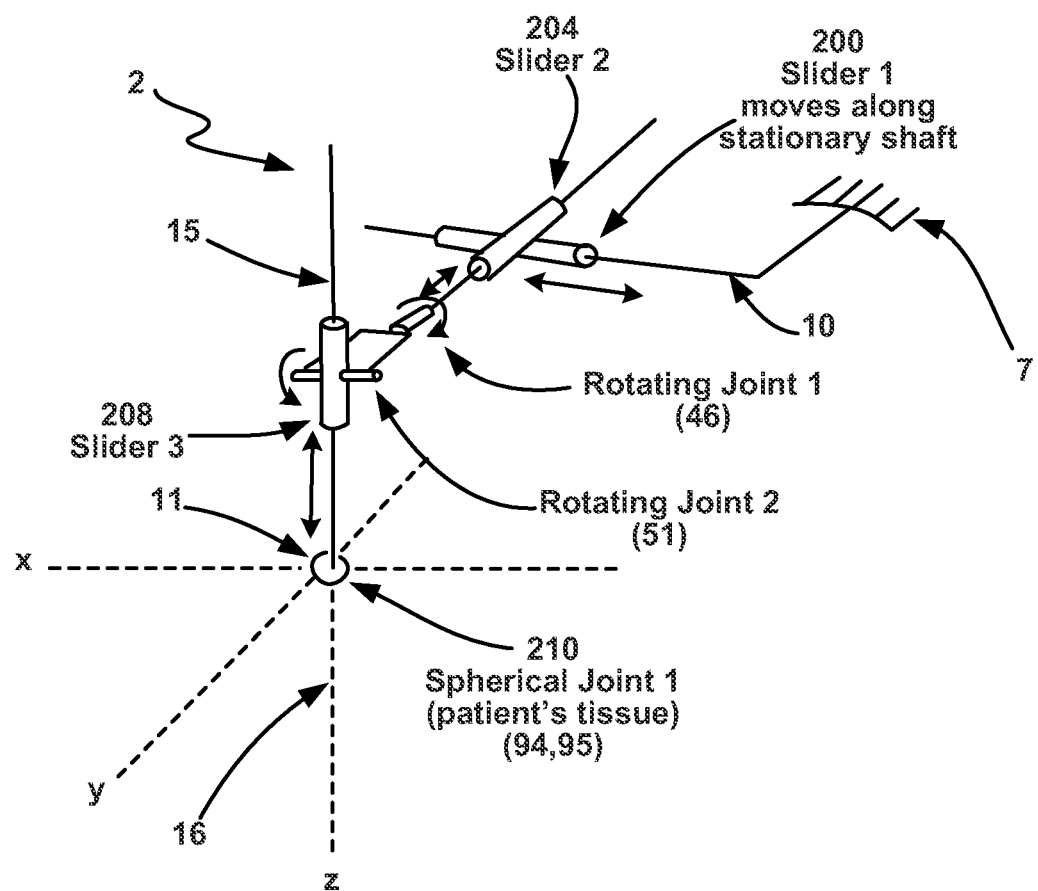
Figure 6C:
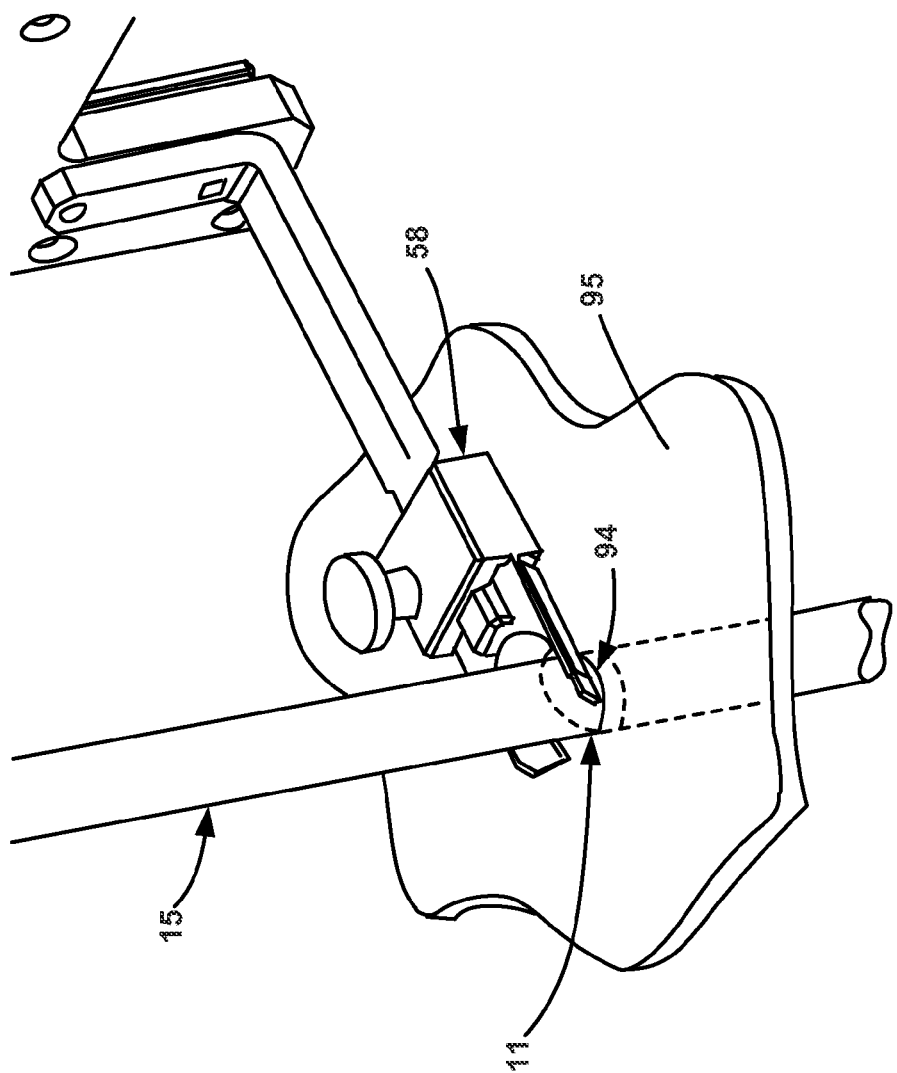

FIG. 6b shows a schematic depiction that more clearly shows the movable elements of an embodiment of the positioning mechanism 2. In the depicted embodiment, the mechanism consists of a novel arrangement of three sliders, two rotating joints, and one spherical joint. A first slider 200 is mounted on adjustable arm 10, connected to support structure 7. A second slider 204 is mounted on first slider 200. A first rotating joint 46 is mounted on the second slider 204. A second rotating joint 51 is mounted on first rotating joint 46. A third slider 208 is mounted on second rotating joint 51. Spherical joint 210 is formed by the incision 94 in the patient's tissue 95 (as depicted in FIG. 6C). The transverse motion first slider 200 is transmitted, via second slider 204 and first (46) and second (51) rotating joints, to third slider 208. This motion causes instrument 15 to pivot about incision 94, driving distal tip 16 in a direction opposite to the movement of the first slider. Similarly, transverse motion on second slider 204 is transmitted via first (46) and second (51) rotating joints to third slider 208. This motion causes instrument 15 to pivot about incision 94, driving distal tip 16 in a direction opposite to the movement of the second slider 204. Transverse motion of third slider 208 either extends the instrument 15 further into incision 94 or retracts the instrument further out of incision 94.

Because non-rigid pivot bearings 46 and 51 are free to move, a second pivot device is required at point 11 to force the instrument to pivot about this point. In a preferred embodiment the tissue of the patient acts as a pivot bearing, allowing instrument 15 to tilt about point 11. This embodiment is shown most clearly in FIG. 6C. In order to aid the user in locating the positioning mechanism 2 optimally over the incision 94 at point 11 in the patient tissue 95, a guide shoe 58 is provided. During setup the user locates the center of the shoe 58 over the incision 94 at point 11, then inserts the instrument 15 into the incision 94 in patient tissue 95, and attaches it in the extend slide 55 with clamp 56. Such a setup is depicted in FIG. 6A. In another embodiment a spherical bearing (not shown) is provided to create the second pivot bearing, which would be located over the incision at point 11 as well.

Figure 7:
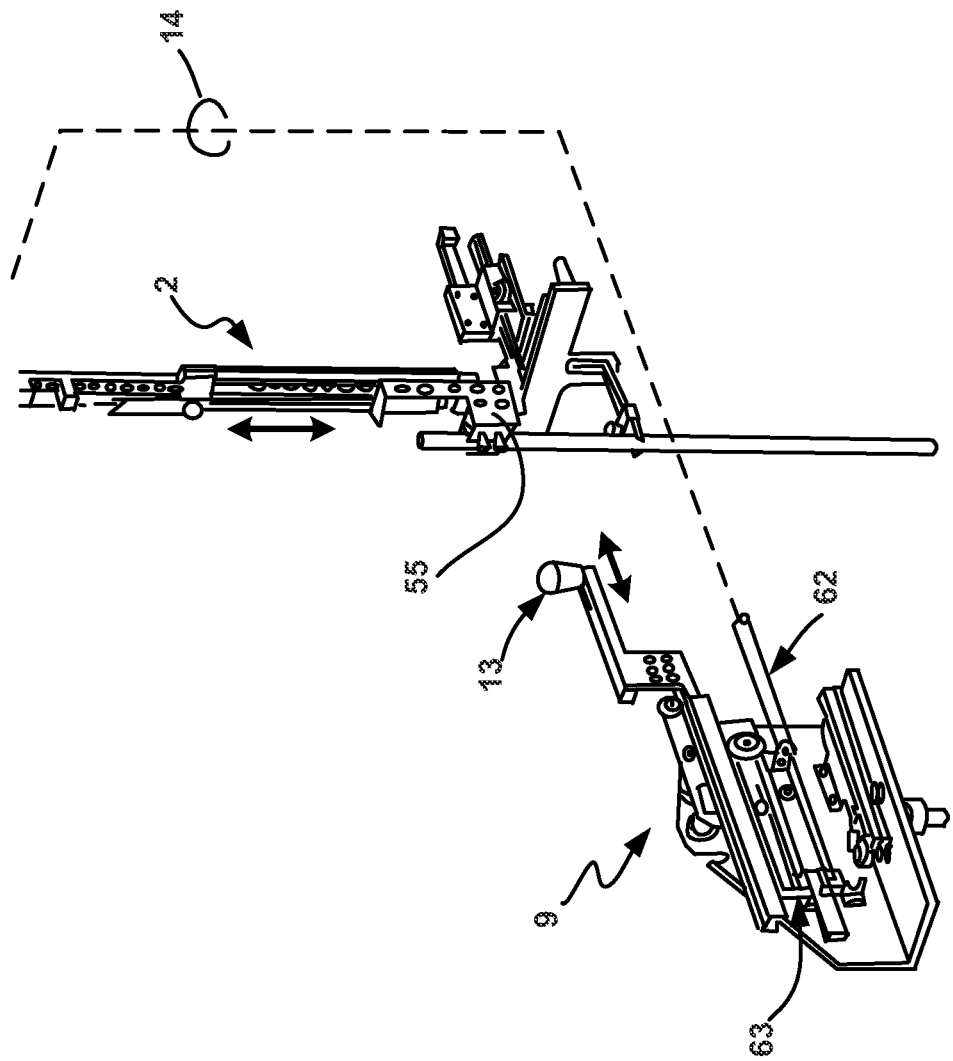
FIG. 7 shows a schematic view of an embodiment of the positioning mechanism and an embodiment of the control mechanism connected by a push-pull cable mechanical-force-transmission connector, in accordance with the present technology.

Referring to FIG. 7, an alternative embodiment is shown. In this embodiment, the mechanical force transmission connector 14 is a system of push-pull cable assemblies. Basic push-pull cable assemblies are well known in the art. Generally, push-pull cable assemblies comprise a flexible cable carried within a flexible guide tube. By pushing or pulling on one end of the cable, motion is transmitted to the other end of the cable, as is commonly seen in bicycle gear changing mechanisms. By example, in FIG. 7 the extend axis is shown driven by a push-pull cable assembly 62 which is attached to the extend mechanism 63 in control handle 9 and to the extend slide 55 in positioning mechanism 2. By pushing/pulling the knob 13 the cable in cable assembly 62 is pushed/pulled, causing the extend slide 55 in positioning mechanism 2 to move in response.

Figure 8:
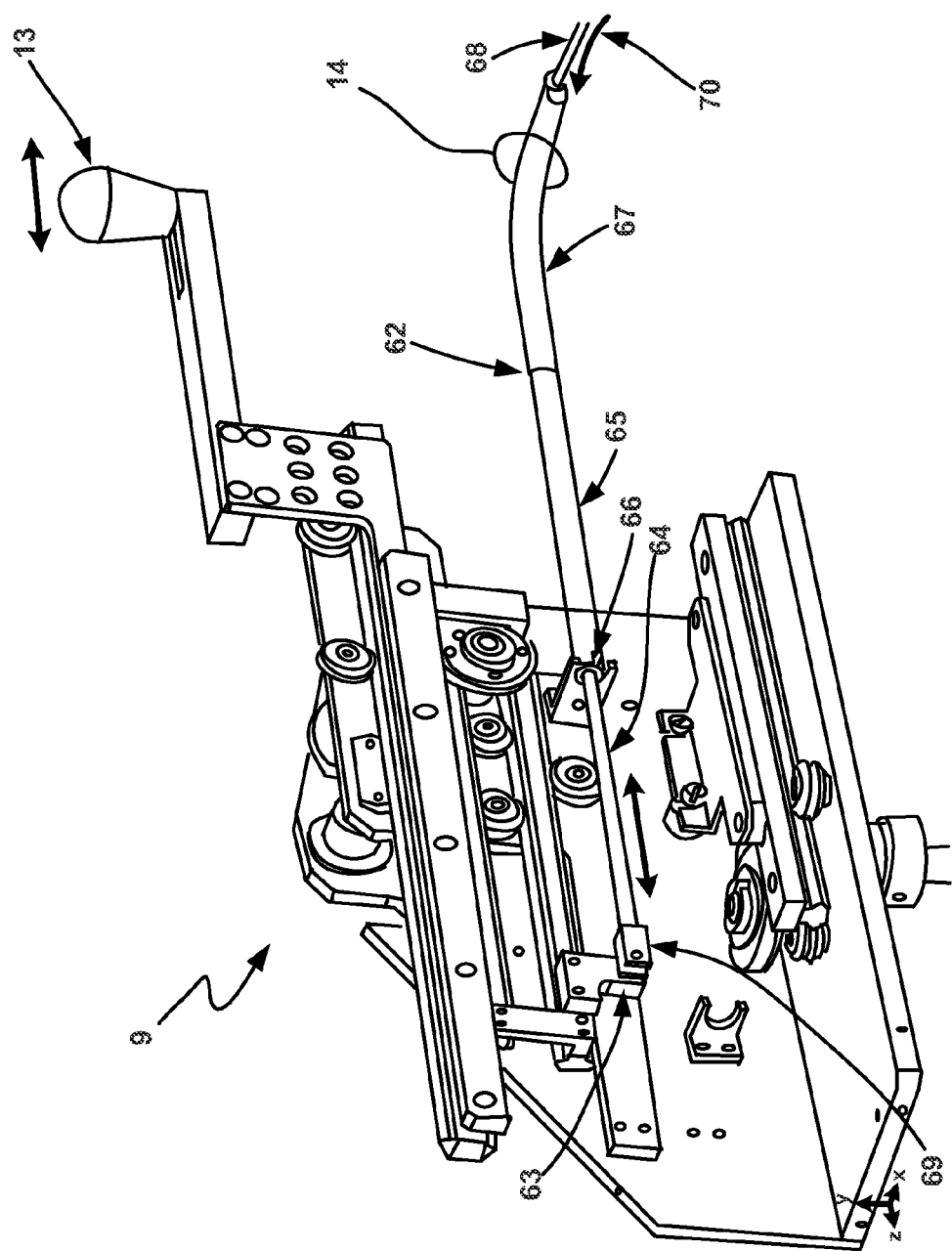
FIG. 8 shows a close-up schematic view of an embodiment of the control mechanism that utilizes a push-pull cable mechanical-force-transmission connector, in accordance with the present technology.

FIG. 8 shows more detail of the push-pull cable used in the extend axis of control handle 9. Push-pull assembly 62 comprises a rigid shaft 64 that is anchored to the extend mechanism 63 by coupling 69. As knob 13 is pushed-pulled, the extend mechanism 63 pushes or pulls on shaft 64 via, coupling 69. Shaft 64 is pushed-pulled into housing 65. Within housing 65 the shaft 64 is connected to flexible cable 68, which slides within flexible guide 67. The resulting motion of cable 68 is indicated by arrow 70.

Figure 9:
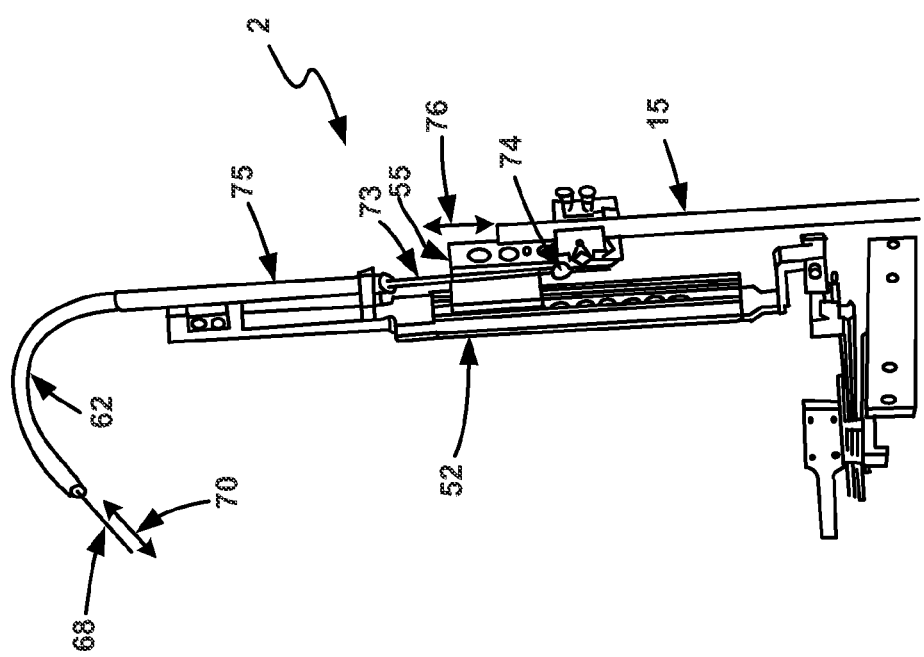
FIG. 9 shows a close-up schematic view of an embodiment of the positioning mechanism that utilizes a push-pull cable mechanical-force-transmission connector, in accordance with the present technology.

Referring now to FIG. 9, the cable assembly 62 terminates at the instrument slide assembly 52 of the positioning mechanism 2. The motion of the flexible cable 68, indicated by arrow 70, is transmitted to the extend slide 55 by rigid shaft 73. The resulting motion of extend slide 55 is indicated by arrow 76.

For clarity and simplicity FIGS. 7, 8, and 9 show only the extend axis driven by a push-pull cable assembly, but this technology contemplates that all motion axes described herein could be similarly be driven with push-pull cables.

Figure 10:
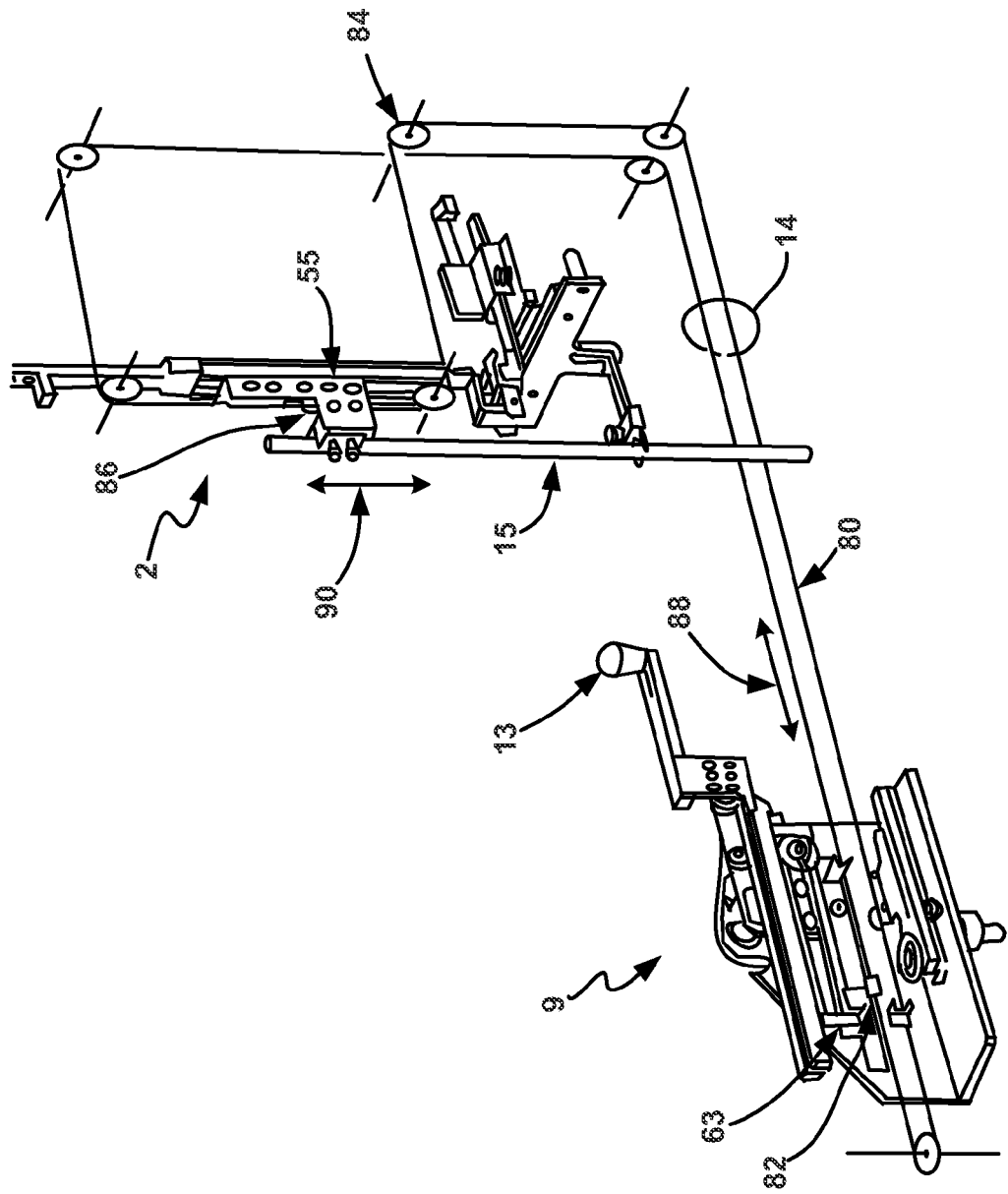
FIG. 10 shows a schematic view of an embodiment of the positioning mechanism and an embodiment of the control mechanism connected by a system of cables and pulleys, in accordance with the present technology.

Another embodiment is shown in FIG. 10. In this embodiment the mechanical force transmission connector 14 is a system of cables and pulleys, shown in semi-schematic form. FIG. 10 depicts the extend axis driven by a cable/pulley arrangement. A flexible cable 80 is attached to the extend mechanism 63 on control handle 9 at coupling 82. Cable 80 is directed around several pulleys 84 to connect the extend mechanism 63 of the control handle 9 to the extend slide 55 on the positioning mechanism 2 at coupling 86. Motion of the extend mechanism 63 results in motion of the cable 80 as shown by arrow 88. This motion is transmitted to the extend slide 55 by cable 80, resulting in motion of the instrument 15 shown by arrow 90.

For clarity and simplicity FIG. 10 shows only the extend axis driven by a cable/pulley arrangement, but this technology contemplates that all motion axes described herein could be similarly driven with cable/pulley arrangements.

This technology also contemplates the use of other mechanical force transmission connections. For example, this technology includes devices utilizing rigid rods connected by universal joints and couplings, push-pull tapes, belts, chains, and ball drives.

Figure 11A:
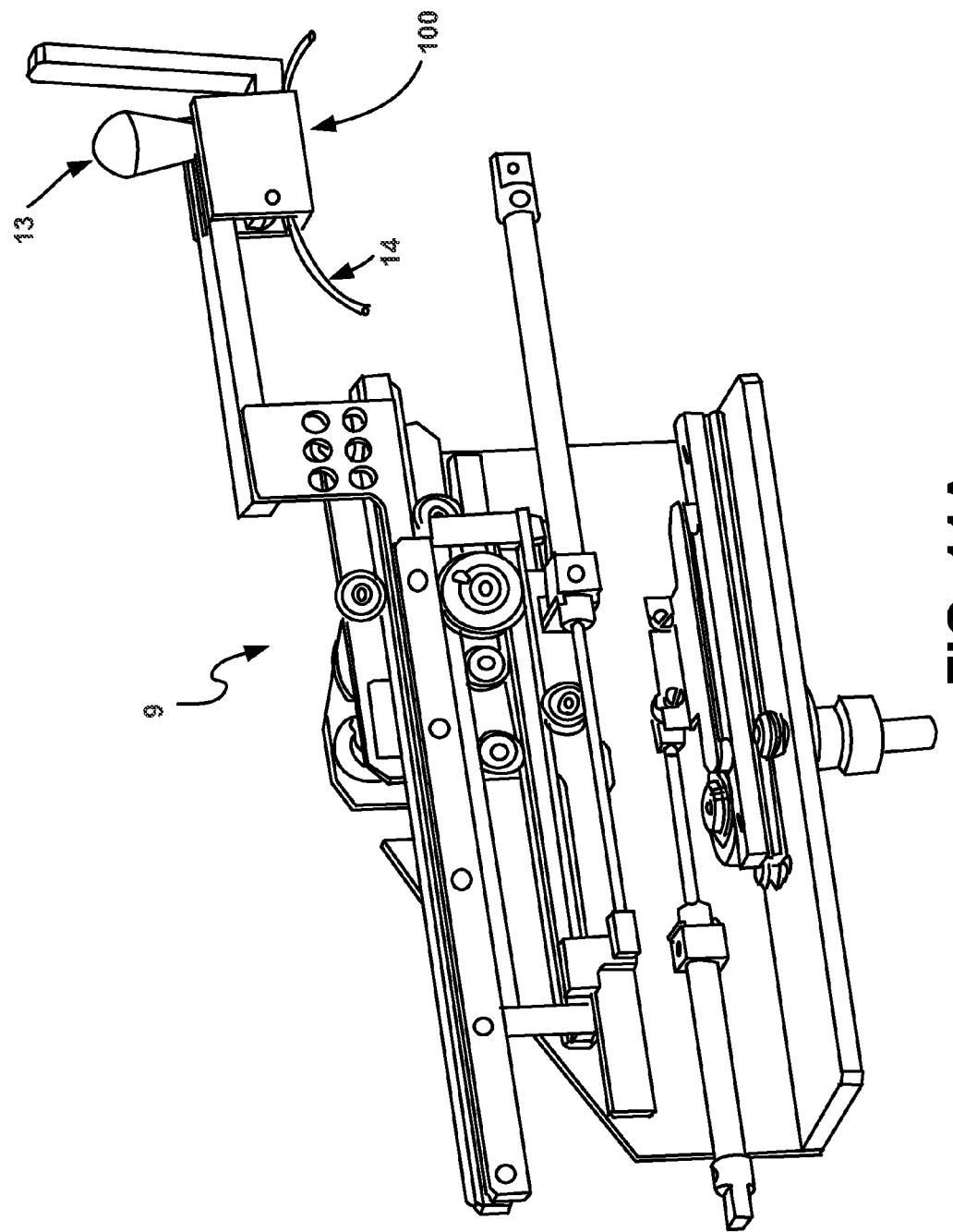
Figure 11B:
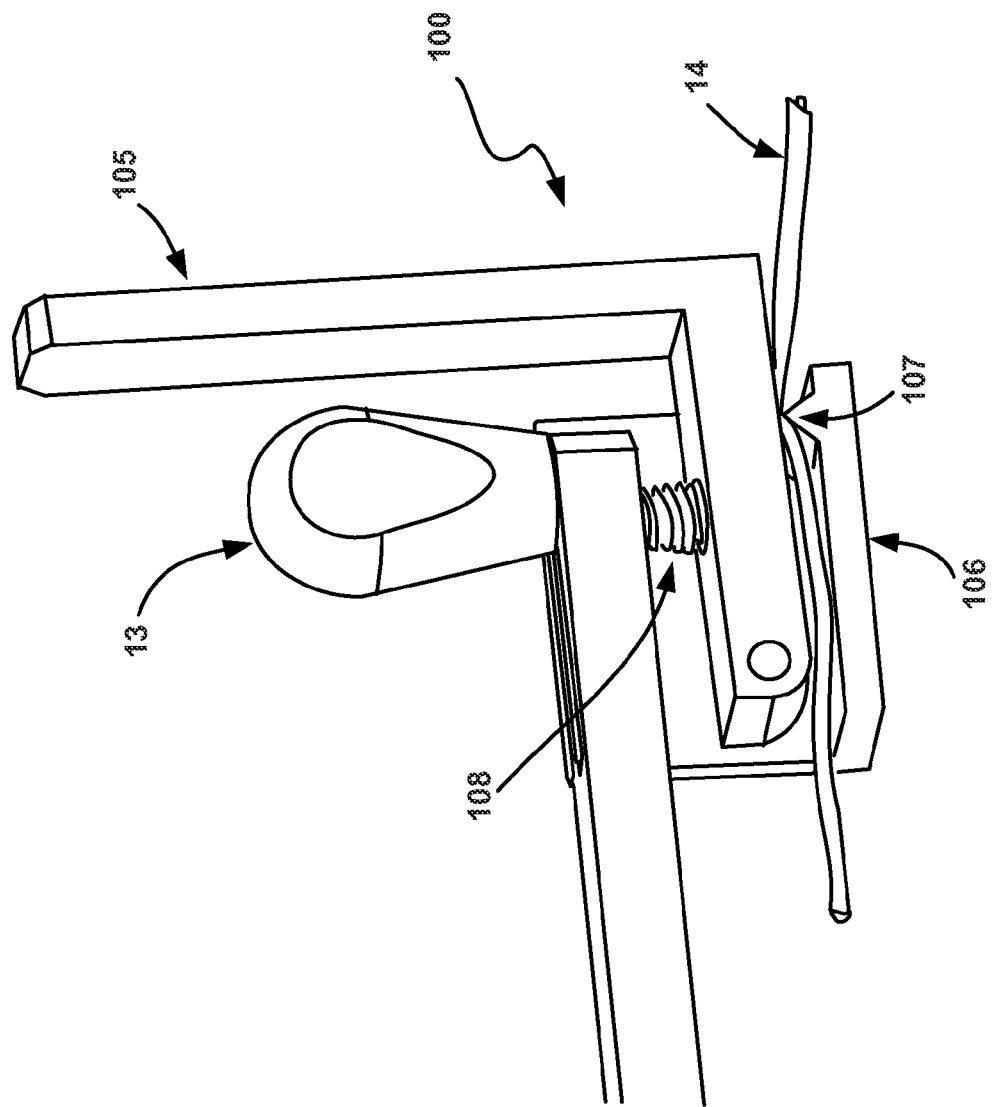

Other embodiments are illustrated in FIGS. 11a-b. Referring to FIG. 11a, a brake mechanism 100 is shown attached to the control handle 9. In the depicted embodiment, the brake 100 is normally on, i.e. the brake is active and preventing motion, unless deactivated by the user. To reposition the instrument, the user grasps the brake mechanism 100, applies force to deactivate the brake, and repositions the instrument. When the new position is reached the user releases the brake mechanism 100, thus reactivating the brake.

Referring to FIG. 11b, an embodiment of the brake mechanism 100 is shown, with one wall removed for clarity, in the actuated position. In this embodiment, the mechanical three transmission connector is hydraulic, but it is contemplated that a brake mechanism could be used with embodiments having any mechanical force transmission connector (for example, one utilizing push-pull cables or cable and pulley systems). In this embodiment, hydraulic tubing 14 (only one tube is shown for clarity) is pinched between pinch point 107 on brake housing 106 and brake lever 105 due to force applied by spring 108. Flow of hydraulic fluid through tubing 14 is thereby prevented, thus preventing motion of the instrument.

FIG. 11b shows an embodiment of the brake mechanism 100 in the deactivated position. Again, in this embodiment, the mechanical force transmission connector is hydraulic, but it is contemplated that a brake mechanism could be used with embodiments having any mechanical force transmission connector (for example, one utilizing push-pull cables or cable and pulley systems). The brake lever 105 has been pulled back toward knob 13, compressing spring 108 and causing brake lever 105 to rotate away from pinch point 107, thereby releasing pressure on, and allowing flow through, tubing 14. In this position motion is allowed and the instrument can be repositioned.

Figure 12:
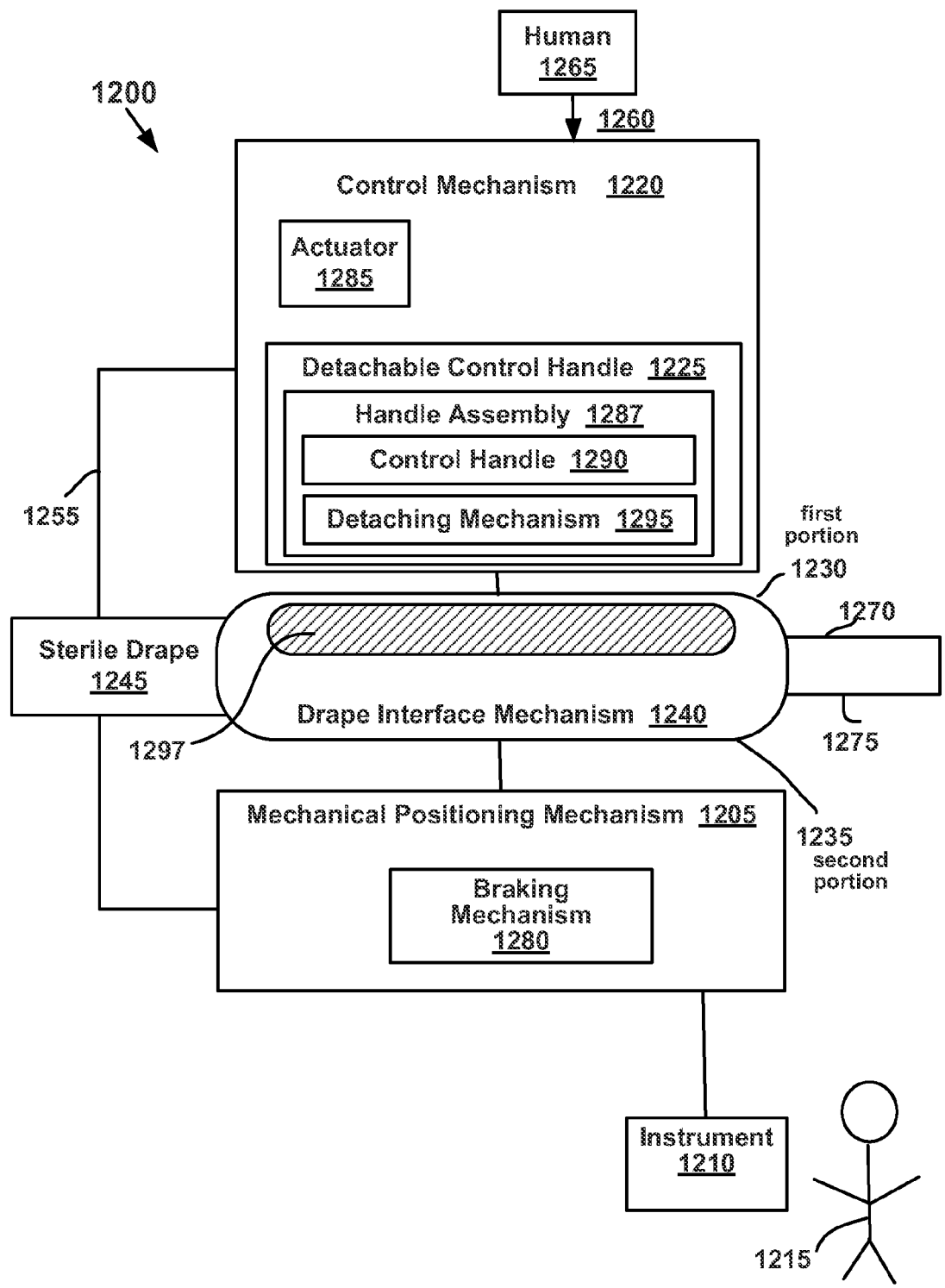
FIG. 12 shows a block diagram of a surgical device for use in positioning an instrument for use in a surgical procedure, in accordance with embodiments of the present technology.

Referring now to FIG. 12, a block diagram of a surgical device 1200 for use in positioning an instrument 1210 for use in a surgical procedure is shown in accordance with embodiments of the present technology. The surgical device 1200 includes a mechanical positioning mechanism 1205, a control mechanism 1220 and a connector 1255.

In one embodiment, the mechanical positioning mechanism 1205 is configured to couple with instrument 1210 outside of a patient's body 1215 and to move the instrument 1210 relative to the patient's body 1215.

Further, in one embodiment, the control mechanism 1220 comprises a detachable control handle 1225 configured to be detachably coupled with the mechanical positioning mechanism 1205. The mechanical positioning mechanism 1205 and the control mechanism 1220 are sealingly coupled with a first portion 1230 and a second portion 1235 of a drape interface mechanism 1240 of a sterile drape 1245, respectively. The sterile drape 1245 is configured for isolating a portion of the surgical device 1200 within a sterile environment. For example, but not limited to, as shown in FIG. 12, the mechanical positioning mechanism 1205 is on the side of the sterile drape 1245 as the patient's body 1215 and "isolated" from the control mechanism 1220 on the opposite side of the sterile drape 1245. The portion of the surgical device 1200 that is isolated is intended to remain as sterile as possible during the functioning of the surgical device 1200.

In one embodiment, the function of the sterile drape 1245 is to keep the fluids within the control mechanism from being contaminated by and from contaminating other areas of the surgical device 1200.

In one embodiment, "sealingly coupled" refers to a coupling in which a seal is formed between a first and a second component of the surgical device 1200. The seal prevents movement of fluids and other matter from one area to another through the seal.

In one embodiment, a connector 1255 is operatively coupled with the control mechanism 1220 and the mechanical positioning mechanism 1205. The control mechanism 1220 is configured for causing the mechanical positioning mechanism 1205 to move the instrument 1210 by transmitting force 1260 applied by a human 1265 to the control mechanism 1220 through the connector 1255.

In one embodiment, the connector 1255 travels through the sterile drape 1255 the a drape interface mechanism 1240 providing a seal to engage the connector 1255, without letting any other material pass through the seal. In another embodiment, the connector 1255 travels around the sterile drape 1245 to connect with the mechanical positioning mechanism 1205. The connector may be made from any material capable of carrying hydraulic fluid, or retaining cables within, the distance from the control mechanism 1220 to the mechanical positioning mechanism 1205. This distance may vary. For example, but not limited to, in one embodiment, this distance may be that of a few feet. While in another embodiment, the distance may be that of a few yards.

In one embodiment, the first portion 1230 of the drape interface mechanism 1240 is positioned on a first surface 1270 of the sterile drape 1245. In one embodiment, the second portion 1235 of the drape interface mechanism 1240 is positioned on a second surface 1275 opposite the first surface 1270 of the sterile drape 1245.

Sterile drape 1245 may be coupled with the drape interface mechanism 1240 by any number of attachment locations and means. For example, the sterile drape 1245 may be attached to the outer edges of the drape interface mechanism 1240 through a type of adhesive. Furthermore, the sterile drape 1245 may be manufactured to be such that an edge closest to the drape interface mechanism 1240 is wedged and sealed in between the first portion 1230 and the second portion 1235 of the drape interlace mechanism 1240.

Significantly, the drape interface mechanism 1240 is formed as part of the sterile drape 1245 such that a seal is formed between the drape interface mechanism 1240 and the sterile drape 1245. In one embodiment, the drape interface mechanism 1240 is designed such that it may receive a specific component or components of the surgical device 1200. These components may be attached, detached, and reattached to the sterile drape 1245.

For example, one component that may be attached detached, and then reattached is the detachable control handle 1225. After being used, the detachable control handle 1225 may be detached, washed, sterilized, and then reattached to the sterile drape 1245.

In one embodiment, the connector 1255 operatively couples with the control mechanism 1220 through the drape interface mechanism 1240. For example, the connector 1255 carries there within a communication of a desired movement, as directed by the control mechanism in combination with the movement of hydraulic fluid within the control and slave cylinders. In another embodiment, the connector 1255 operatively couples with the control mechanism 1220 around the sterile drape 1245. The connector 1255 may be just long enough to make it around the sterile drape 1245 that covers the control mechanism 1220, or it may even be long enough to stretch from one room to another.

In one embodiment, the connector 1255 comprises a hydraulic system. In another embodiment, the connector 1255 comprises a closed-loop hydraulic system. In yet another embodiment, the connector 1255 comprises a push-pull cable system. In another embodiment, the connector 1255 comprises a cable and pulley system. Furthermore, in one embodiment, the connector 1255 includes more than one of a hydraulic system, a push-pull cable system, and a cable and pulley system.

In one embodiment, the mechanical positioning mechanism 1205 is configured for utilizing tissue of a patient to create a pivot point for positioning of the instrument 1210 within the patient's body 1215. For example, but not limited to, a portion of the mechanical positioning mechanism 1205 may be attached to a patient's skin as a foundation for movement. In one example, the attachment is by means of an adhesive. The portion of the mechanical positioning mechanism 1205 holding an instrument, may then pivot, using the foundation as a set point, and swing the instrument from a first location to a second location in the patient's body 1215.

In another embodiment, the mechanical positioning mechanism 1205 comprises non-rigid pivot elements. In yet another embodiment, the mechanical positioning mechanism 1205 comprises a braking mechanism 1280 for locking the instrument 1210 into a particular position, and wherein the control mechanism 1220 comprises an actuator 1285 for the braking mechanism 1280.

Referring still to FIG. 2, a detachable control handle 1225 of a surgical device 1200 for use in positioning an instrument 1210 for us in a surgical procedure is shown according to one embodiment of the present technology. In one embodiment, the detachable control handle 1225 comprises a handle assembly 1287 for communicating with a mechanical positioning mechanism 1205 via a connector 1255. The mechanical positioning mechanism 1205 is configured to couple with the instrument 1210 outside of a patient's body 1215 and to move the instrument 1210 relative to the patient's body 1215.

In one embodiment, the handle assembly 1287 comprises a control handle 1290 and a detaching mechanism 1295 coupled with the control handle 1290. The detaching mechanism 1295 is configured for detachably coupling the control handle 1290 with the mechanical positioning mechanism 1205. The control handle 1290 and the mechanical positioning mechanism 1205 are sealingly coupled with a first 1230 and a second 1235 portion of a drape interface mechanism 1240 of a sterile drape 1245, respectively. The sterile drape 1245 is configured for isolating a portion of the surgical device 1200 within a sterile environment.

In one embodiment, the control handle 1290 and the detaching mechanism 1295 comprise a single component. For example, the control handle 1290 and the detaching mechanism 1295 may be manufactured as one piece, such that just a portion of the control handle 1290 is operable to attach to and detach from the drape interface mechanism 1240. In another embodiment, the detaching mechanism 1295 is detachably coupled with the control handle 1290. For example, the control handle 1290 and the detaching mechanism 1295 may be manufactured as two separate pieces such that they may be separated from each other and then reattached or replaced by another attachable piece.

Figure 13:
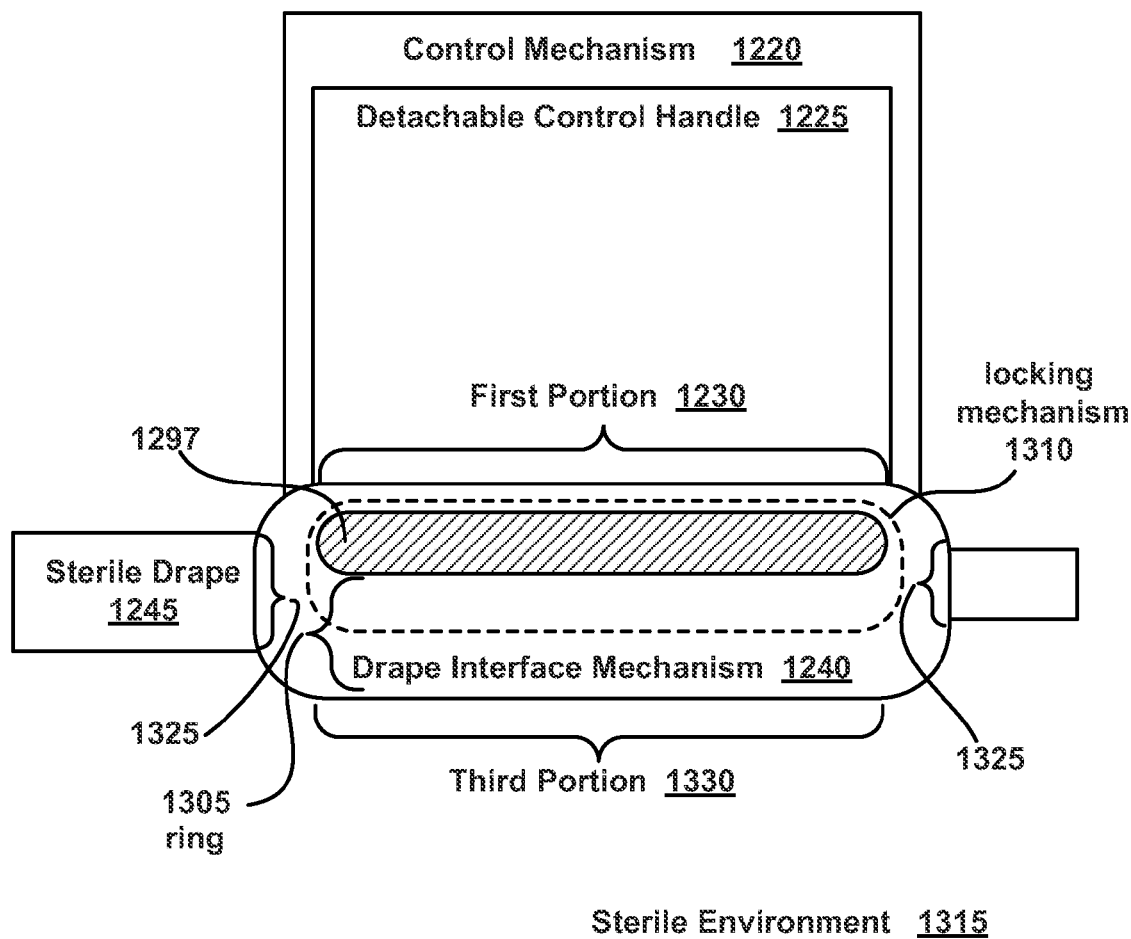
FIG. 13 shows a block diagram of a surgical device for use in a surgical procedure, in accordance with embodiments of the present technology.

Referring now to both FIG. 12 and FIG. 13, in one embodiment, the surgical device 1300 comprises a mechanical positioning mechanism 1205, a control mechanism 1220, a drape interface mechanism 1240 and a connector 1255. The mechanical positioning mechanism 1205 is configured to couple with an instrument 1210 outside of a patient's body 1215 and to move the instrument 1210 to the patient's body 1215. The control mechanism 1220 comprises a detachable control handle 1290 configured to be detachable coupled with the mechanical positioning mechanism 1205.

In one embodiment, the drape interface mechanism 1240 sealingly couples the mechanical positioning mechanism 1205 and the control mechanism 1220 with a sterile drape 1245. The sterile drape 1245 is configured for isolating a portion of the surgical device 1300 within a sterile environment 11315. The drape interface mechanism 1240 comprises a ring 1305 defining an opening 1297 through the sterile drape 1245 and is configured for sealingly receiving and retaining there within a portion of the mechanical positioning mechanism 1205 and a portion of the control mechanism 1220. For example, instead of the mechanical positioning mechanism 1205 and the control mechanism 1220 coupling with the drape interface mechanism 1240 through an attachment means, an end portion of the mechanical positioning mechanism 1205 and the control mechanism 1220 may be placed within the drape interface mechanism 1240 and coupled therein. In this case, the drape interface mechanism 1240 will be such that it provides a tight seal around the edges of an object placed therein.

In one example, but not limited to, the drape interface mechanism 1240 may be formed such that a set of sealable material is connected to the opposing surfaces of the drape interface mechanism 1240, the material having a small hole therein. A portion of the control mechanism 1220 may then be wedged through the hole and lie within the interior of the drape interface mechanism 1240. Similarly, a portion of the mechanical positioning mechanism 1205 may be wedged through the hole in the material lying on the opposite side of the drape interface mechanism 1240 and also be attached to the control mechanism 1220 while lying within the drape interface mechanism 1240. In this manner, the mechanical positioning mechanism 1205 and the control mechanism 1220 are able to be coupled with each other without becoming part of each other's sterilized or unsterilized environment.

In one embodiment, the connector 1255 is operatively coupled with the control mechanism 1220 and the positioning mechanism 1205. The control mechanism 1220 is configured for causing the positioning mechanism 1205 to move the instrument 1210 by transmitting force 1260 applied by a human 1265 to the control mechanism 1220 through the connector 1255.

Referring still to FIGS. 12 and 13, a surgical device comprising a drape interface mechanism 1240 is shown in accordance with embodiments of the present technology. In one embodiment, the drape interface mechanism 1240 is configured for sealingly coupling a detachable control handle 1225 of a control mechanism 1220 with a sterile drape 1245. The sterile drape 1245 is configured for isolating a portion of the surgical device 1200/1300 within a sterile environment. The drape interface mechanism 1240 comprises a ring 1305 defining an opening 1297 through the sterile drape 1245.

In one embodiment, the ring 1305 comprises a first portion 1230 and a second portion 1325. The first portion 1230 is configured for detachably and sealingly coupling with the control mechanism 1220. The second portion 1325 is configured for sealingly coupling with the sterile drape 1245.

In one embodiment, the drape interface mechanism 1240 is waterproof in another embodiment the second portion 1325 comprises a locking mechanism 1310 configured for detachably coupling the ring 1305 with the detachable control handle 1225.

In one embodiment, the detachable control handle 1225 comprises a handle assembly 1287 configured for communicating with a mechanical positioning mechanism 1205 via a connector 1255, wherein the mechanical positioning mechanism 1205 is configured to couple with the instrument 1210 outside of a patient's body 1215 and to move the instrument 1210 relative to the patient's body 1215.

In one embodiment, the handle assembly 1287 comprises a control handle 1290, a detaching mechanism 1295 coupled with the control handle 1290. The detaching mechanism 1295 is configured for detachably coupling the control handle 1290 with the mechanical positioning mechanism 1205, wherein the control handle 1290 and the mechanical positioning mechanism 1205 are sealingly coupled with the first portion 1230 and a third portion 1330 of the drape interface mechanism 1240, respectively, wherein the sterile drape 1245 is configured for isolating a portion of the surgical device 1200/1100 within a sterile environment.

In one embodiment, the ring 1305 is round. In another embodiment, the ring 1305 is square. It should be appreciated, that the ring 1305 may be any shape that defines an opening 1297. In one embodiment the control handle 1290 and the detaching mechanism 1295 comprise a single component. In another embodiment, the control handle 1290 and the detaching mechanism 1295 comprise separate detachable components.

In one embodiment, and referring still to FIGS. 12 and 13, a surgical device 1200 is shown comprising a mechanical positioning mechanism 1205, a control mechanism 1220 and a connector 1255. The mechanical positioning mechanism 1205 is configured to couple with an instrument 1210 outside of a patient's body 1215 and to move the instrument 1210 relative to the patient's body 1215. The control mechanism 1220 comprises a detachable control handle 1290 configured to be detachably coupled with the mechanical positioning mechanism 1205. The detachable control handle is sealingly coupled with the drape interface mechanism 1240 of a sterile drape. The sterile drape 1245 is configured for isolating a portion of the surgical device within a sterile environment. The drape interface mechanism 1240 comprises a ring 1305 defining an opening 1297 through the sterile drape 1245.

In one embodiment, the ring 1305 comprises a first portion 1230 and a second portion 1325. The first portion 1230 is configured for detachably and sealingly coupling with the control mechanism 1220. The second portion 1325 is configured for sealingly coupling with the sterile drape 1245.

In one embodiment, the connector 1255 is operatively couple with the control mechanism 1220 and the mechanical positioning mechanism 1205. The control mechanism 1220 is configured for causing the mechanical positioning mechanism 1205 to move the instrument 1210 by transmitting force 1260 applied by a human 1265 to the control mechanism 1220 through the connector 1255.

Further, in one embodiment and as describe herein, the control handle 1290 comprises a handle assembly 1287 configured for communicating with the mechanical positioning mechanism 1205 via a connector 1255. The handle assembly 1287 comprises a control handle 1290 and a detaching mechanism 1295, as described herein.

In one embodiment, the connector 1255 operatively couples the control mechanism 1220 with the mechanical positioning mechanism 1205 by hydraulic communication through the drape interface mechanism 1205. In another embodiment, the connector 1255 operatively couples the control mechanism 1220 with the mechanical positioning mechanism 1205 by a cable and pulley system through the drape interface mechanism 1240. In yet another embodiment, the connector 1255 operatively couples the control mechanism 1220 with the mechanical positioning mechanism 1205 by a push-pull cable system.

In yet another embodiment, the connector 1255 operatively couples the control mechanism 1220 with the mechanical positioning mechanism 1205 by a connection around the sterile drape 1245.

Figure 14:
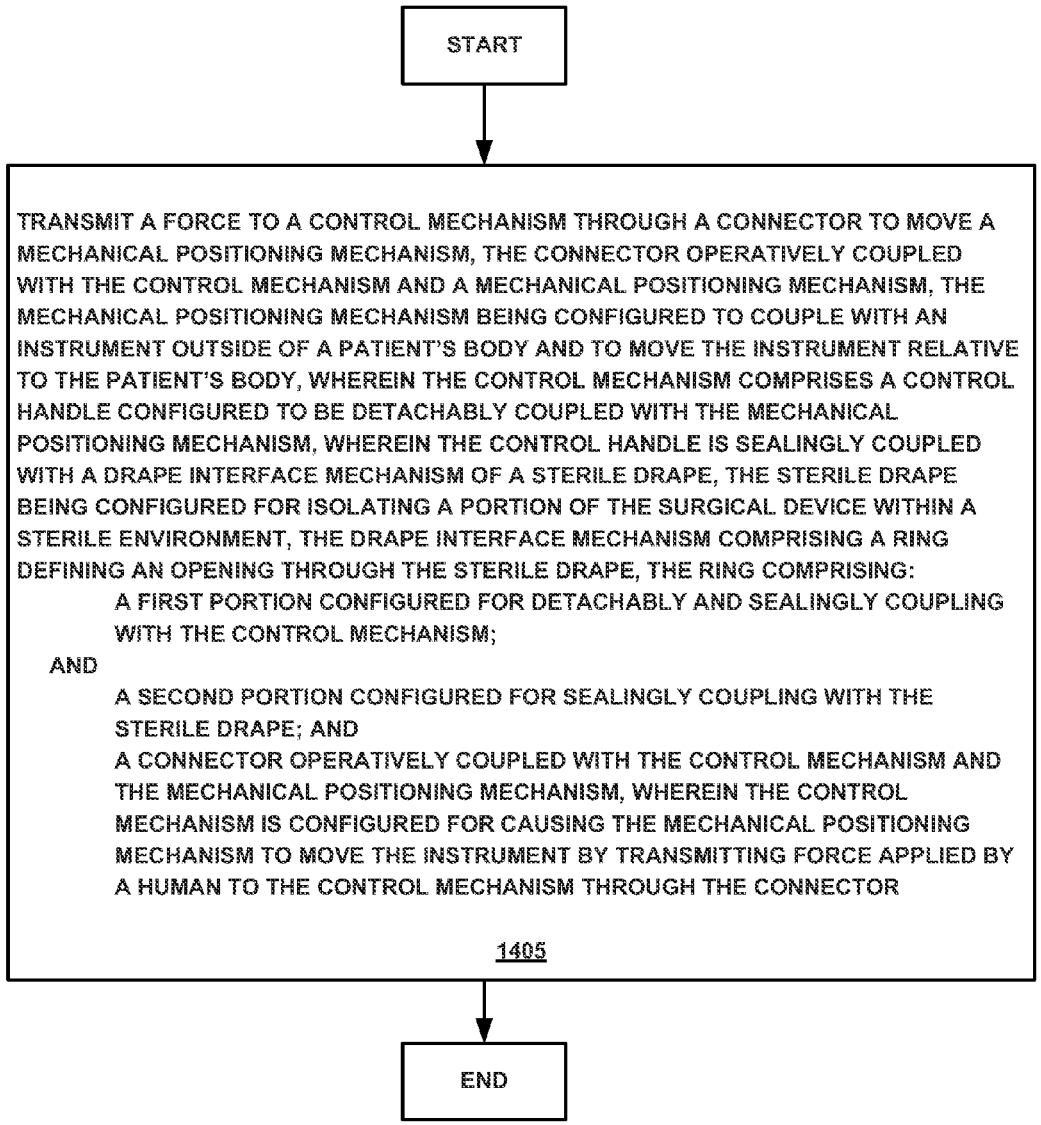
FIG. 14 shows a flowchart of a method for using a surgical device, in accordance with embodiments of the present technology.

Referring now to FIG. 14, a flowchart 1400 of a method for using a surgical device is shown in accordance with embodiments of the present technology. Referring now to 1405 of FIG. 14, in one embodiment, a force 1260 is transmitted to a control mechanism 1220 through a connector 1255 to move a mechanical positioning mechanism 1205, the connector 1255 operatively coupled with the control mechanism 1220 and a mechanical positioning mechanism 1205, the mechanical positioning mechanism 1205 being configured to couple with an instrument 1210 outside of a patient's body 1215 and to move the instrument 1210 relative to the patient's body 1215, wherein the control mechanism 1220 comprises a control handle 1290 configured to be detachably coupled with said mechanical positioning mechanism 1205, wherein control handle 1290 is sealingly coupled with a drape interface mechanism 1240 of a sterile drape 1245, the sterile drape 1245 being configured for isolating a portion of the surgical device 1200 within a sterile environment, the drape interface mechanism 1240 comprising a ring 1305 defining an opening 1297 through the sterile drape 1245.

In one embodiment, the ring 1305 comprises a first portion 1230, a second portion 1325 and a connector 1255. The first portion 1230 is configured for detachably and sealingly coupling with the control mechanism 1220. The second portion 1325 is configured for sealingly coupling with the sterile drape 1245. The connector 1255 is operatively coupled with the control mechanism 1220 and the mechanical positioning mechanism 1205, wherein the control mechanism 1220 is configured for causing the mechanical positing mechanism 1205 to move the instrument 1210 by transmitting force applied by a human to the control mechanism through the connector.

Although the subject matter has been described in a language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A surgical device for use in positioning an instrument for use in a surgical procedure, said surgical device comprising:
    a mechanical positioning mechanism configured to couple with an instrument outside of a patient's body and to move said instrument relative to said patient's body;
    a control mechanism comprising a detachable control handle configured to be detachably coupled with said mechanical positioning mechanism, wherein said control mechanism and said mechanical positioning mechanism are sealingly coupled with a first and second portion of a drape interface mechanism of a sterile drape, respectively, wherein said sterile drape is configured for isolating a portion of said surgical device within a sterile environment;
    a connector operatively coupled with said control mechanism and said mechanical positioning mechanism, wherein said control mechanism is configured for causing said mechanical positioning mechanism to move said instrument by transmitting applied force to said control mechanism through said connector.

2. The surgical device of claim 1, wherein said first portion of said drape interface mechanism is positioned on a first surface of said sterile drape, and said second portion of said drape interface mechanism is positioned on a second surface of said sterile drape opposite said first surface.

3. The surgical device of claim 1, wherein said connector operatively couples with said control mechanism through said drape interface mechanism.

4. The surgical device of claim 3, wherein said connector is configured for carrying there within a communication of a desired movement, said desired movement directed by said control mechanism and a movement of hydraulic fluid.

5. The surgical device of claim 1, wherein said connector operatively couples with said control mechanism around said sterile drape.

6. The surgical device of claim 1, wherein said connector comprises a hydraulic system.

7. The surgical device of claim 6, wherein said hydraulic system comprises a closed-loop hydraulic system.

8. The surgical device of claim 1, wherein said connector comprises a push-pull cable system.

9. The surgical device of claim 1, wherein said connector comprises a cable and pulley system.

10. The surgical device of claim 1, wherein said connector includes more than one of a hydraulic system, a push-pull cable system, and a cable and pulley system.

11. The surgical device of claim 1, wherein said mechanical positioning mechanism is configured for utilizing tissue of a patient to create a pivot point for positioning of said instrument within said patient's body.

12. The surgical device of claim 1, wherein said mechanical positioning mechanism comprises non-rigid pivot elements.

13. The surgical device of claim 1, wherein said mechanical positioning mechanism comprises a braking mechanism configured for locking said instrument into a particular position, and wherein said control mechanism comprises an actuator for said braking mechanism.

* * * * *